(12) United States Patent
Schroeder et al.

(10) Patent No.: US 6,384,026 B1
(45) Date of Patent: May 7, 2002

(54) MACROCYCLIC POLYAMINE LACTONES AND DERIVATIVES THEREOF AND THEIR USE AS ARTHROPOD REPELLENTS

(75) Inventors: Frank C. Schroeder, Ithaca; Jay J. Farmer, Brooklyn; Thomas Eisner, Ithaca, all of NY (US); Scott R. Smedley, Bolton, CT (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/285,474

(22) Filed: Apr. 2, 1999

Related U.S. Application Data

(60) Provisional application No. 60/080,660, filed on Apr. 3, 1998.

(51) Int. Cl.[7] ...................... A01N 43/72; A01N 43/712; C07D 259/00; C07D 273/00
(52) U.S. Cl. .................. 514/183; 514/11; 530/318; 540/454; 540/460; 540/467
(58) Field of Search ................................. 540/454, 460, 540/467; 514/11, 183; 530/318

(56) References Cited

U.S. PATENT DOCUMENTS

| | | | | |
|---|---|---|---|---|
| 4,996,315 A | * | 2/1991 | Speranza et al. | ........... 540/454 |
| 5,532,231 A | * | 7/1996 | Rosenberg | .................. 514/183 |

OTHER PUBLICATIONS

Bradshaw et al., Aza–Crown Macrocycles John Wiley & Sons., Inc., pp. 352,353, 1993.*
Habermehl, "Neurotoxins from Amphibians," *Toxicon*, 29:1165–1166 (1991).
Benoit, "Mechanism(s) of Action of Neurotoxins Acting on the Inactivation of Voltage–Gated Sodium Channels," *C. R. Soc. Biol.*, 192:409–436 (1998).
Brown, "Insights on the Voltage–Sensitive Sodium Channel: The Batrachotoxin Connection," *Toxicon*, 27:21–22 (1989).
Gusovsky et al., "Interaction of Pumiliotocin B With an 'Alkaloid–Binding Domain' on the Voltage–Dependent Sodium Channel," *Molecular Pharmacology*, 42:1104–1108 (1992).
Tang et al., "Effects of Besipirdine at the Voltage–Dependent Sodium Channel," *Br. J. Pharmacol.*, 116:2468–2472 (1995).
Myers et al., "Conus Peptides as Chemical Probes for Receptors and Ion Channels," *Chem. Rev.*, 93:1923–1936 (1993).
Schröder et al., "Combinatorial Chemistry in Insects: A Library of Defensive Macrocyclic Polyamines," *Science*, 281:428–431 (1998).
Giannis et al., "LiBH$_4$(NaBH$_4$)/Me$_3$SiCl, An Unusually Strong and Versatile Reducing Agent," *Angew. Chem. Int. Ed. Engl.*, 28:218–220 (1989).
Mukaiyama et al., "An Efficient Method for the Synthesis of Macrocyclic Lactone," *Chem. Lett.*, 4:441–444 (1977).

\* cited by examiner

*Primary Examiner*—Richard L. Raymond

(57) ABSTRACT

The present invention describes an isolated macrocycle having the formula:

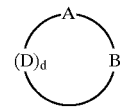

where d is an integer from 0 to about 100; A, B, and each D are the same or different and are selected from the group consisting of

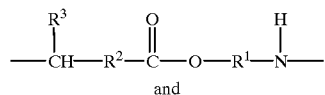

and

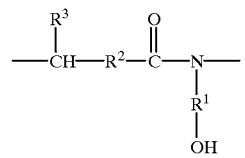

each $R^1$ is the same or different and is a bivalent alkylene moiety; each $R^2$ is the same or different and is a bivalent alkylene moiety; and each $R^3$ is the same or different and is selected from the group consisting of a hydrogen atom and an alkyl moiety. Methods for producing these macrocycles are also described. The macrocycles of the present invention can be used as arthropod repellents.

34 Claims, 8 Drawing Sheets

|   | Dimers | Trimers | Tetramers | Pentamers | Hexamers | Heptamers |
|---|--------|---------|-----------|-----------|----------|-----------|
| M | 454 | 681 | 908 | 1135 | 1362 | 1589 |
|   | 440 | 667 | 894 | 1121 | 1348 | 1575 |
|   | 426 | 653 | 880 | 1107 | 1334 | 1561 |
|   |     | 639 | 866 | 1093 | 1320 |      |
|   |     | 625 | 852 | 1079 | 1306 |      |
|   |     | 611 | 838 | 1065 |      |      |
|   |     | 597 | 824 |      |      |      |
| Σ | 1% | 47% | 37% | 11% | 3% | 1% |

MACROCYCLIC POLYAMINE LACTONES AND DERIVATIVES THEREOF AND THEIR USE AS ARTHROPOD REPELLENTS

This application claims the benefit of U.S. Provisional Patent Application Ser. No. 60/080,660, filed Apr. 3, 1998, incorporated herein by reference.

This invention was made through the support of the National Institutes for Health (Grant Nos. GM53830 and AI2908). The U.S. Government may have certain rights in this invention.

FIELD OF THE INVENTION

The present invention relates to macrocyclic compounds and their derivatives and to methods for synthesizing and using these compounds.

BACKGROUND OF THE INVENTION

Substantial effort has been expended by a wide variety of entities in attempting to develop highly effective pesticides, particularly insecticides and/or insect repellents which are capable of eradicating or controlling arthropods, such as insects, that contaminate stored food, for example, fruits, vegetables, grains, and the like; that destroy ornamental and agricultural plants, crops, and trees; or that attack, harm, or annoy humans and animals. Particularly bothersome for humans and animals are blood-sucking insects, such as mosquitoes, fleas, and lice, and anthropods, such as ticks. These insects, in addition to being an annoyance, are also potentially harmful due to their ability to transmit diseases.

One approach has been to develop poisons which kill the insects. However, in many instances, insects have developed resistance to the pesticides (possibly by "natural selection") or are able to detect and avoid poisons. Furthermore, many poisons have undesirable effects on human and other animal life, and therefore uses thereof have often been regulated or forbidden.

Moreover, some insects, like the common German or house cockroach (Blattela germanica) and the American cockroach (Periplaneta americana), when killed by pesticides and left in areas that cannot be reached or cleaned, have been identified as a significant allergen in house dust. It has been estimated that 10–15 million people in the United States are allergic to cockroaches. Since dead cockroaches in unreachable areas emit the allergen, poisons are ineffective in such situations. Still further, simply the presence of such insects in areas inhabited or occupied by humans is highly undesirable.

In an attempt to avoid the problems posed by the use of insect poisons and to meet the consumer demand, various insect repellent formulations have been developed. However, many such formulations incorporate active ingredients which are highly toxic to humans and to many animals. Consequently, the usable concentration of these toxic chemicals must be reduced, typically to the point of rendering the resulting formulation ineffective in providing the desired repulsive effect. Moreover, many such repellent materials are toxic and others are foul smelling, discoloring, or both. These adverse properties seriously limit their utility in many situations. Insect repellent formulations which have enjoyed commercial success, for example those containing N,N-diethyl-m-toluamide ("DEET"), have been few in number.

Insect pupae, given that they generally cannot crawl, run, or fly, should be vulnerable to predation. However, many benefit from concealment and camouflage, or from mechanical means of defense. It has been discovered that in some cases insect pupae are protected chemically. For example, pupae of coccinellid beetles (genus Epilachna) bear a dense coating of glandular hairs, as shown in FIG. 1, that secrete oily droplets which are repulsive to insects. Likewise, the Mexican bean beetle (*E. varivestis*) secretes azamacrolides, which are lactones with a single nitrogen atom incorporated into a ring of 15 or 16 members, as shown in FIG. 2.

Thus, a need continues to exist for new insect repellents, preferably ones which, unlike DEET, are based on naturally occurring products and which have greater repellent activity against a broader group of insect types, reduced toxicity, longer lasting effects, improved physical characteristics, reduced staining characteristics, and improved stability. The present invention is directed toward meeting this need.

SUMMARY OF THE INVENTION

The present invention is related to an isolated macrocycle having the formula:

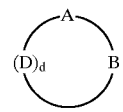

where d is an integer from 0 to about 100; A, B, and each D are the same or different and are selected from the group consisting of

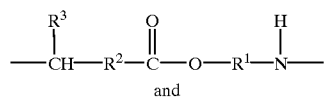

and

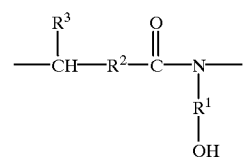

wherein each $R^1$ is the same or different and is a bivalent alkylene moiety; each $R^2$ is the same or different and is a bivalent alkylene moiety; and each $R^3$ is the same or different and is selected from the group consisting of a hydrogen atom and an alkyl moiety.

The present invention also relates to a method of preparing a macrocycle having the formula:

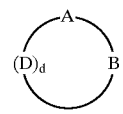

where d is an integer from 0 to about 100; A, B, and each D are the same or different and are selected from the group consisting of

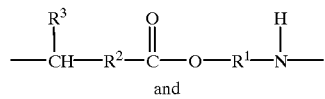

and

-continued $$-CH(R^3)-R^2-C(=O)-N(R^1)-OH$$

where each $R^1$ is the same or different and is a bivalent alkylene moiety; each $R^2$ is the same or different and is a bivalent alkylene moiety; and each $R^3$ is the same or different and is selected from the group consisting of a hydrogen atom and an alkyl moiety. The method includes providing an isolated linear compound having the formula:

$$Y^2-C(=O)-R^4-CH(R^5)-(E)-(F)_f-N(X)-R^6-OY^1$$

where f is an integer from 0 to about 100; E and each F are the same or different and have the formula:

$$-N(X)-R^6-O-C(=O)-R^4-CH(R^5)-$$

where each $R^4$ is the same or different and is a bivalent alkylene moiety; each $R^5$ is the same or different and is selected from the group consisting of a hydrogen atom and an alkyl moiety; each $R^6$ is the same or different and is a bivalent alkylene moiety; each X is the same or different and is hydrogen or an amine protecting group; $Y^1$ is a hydrogen atom or an alcohol protecting group; and $Y^2$ is an OH group or an carboxylic acid protecting group. The method further includes cyclizing the linear compound under conditions effective to produce a macrocycle, wherein A, B, and each D are the same or different and have the formula:

$$-CH(R^3)-R^2-C(=O)-O-R^1-N(H)-$$

The present invention further relates to an isolated linear compound having the formula:

$$Y^2-C(=O)-R^4-CH(R^5)-(E)-(F)_f-N(X)-R^6-OY^1$$

where f is an integer from 0 to about 100; E and each F are the same or different and have the formula:

$$-N(X)-R^6-O-C(=O)-R^4-CH(R^5)-$$

where each $R^4$ is the same or different and is a bivalent alkylene moiety; each $R^5$ is the same or different and is selected from the group consisting of a hydrogen atom and an alkyl moiety; each $R^6$ is the same or different and is a bivalent alkylene moiety; each X is the same or different and is hydrogen or an amine protecting group; $Y^1$ is a hydrogen atom or an alcohol protecting group; and $Y^2$ is an OH group or an carboxylic acid protecting group.

The macrocycles of the present invention or combinations thereof can be used as a substantially pure substance or as a component in compositions or formulations of substances to repel insects or arthropods from the proximity and/or the surfaces of plants, fruits and vegetables, and animals. Further, the macrocycles of the present invention or combinations thereof can be used as a substantially pure substance or as a component in compositions or formulations of substances to repel insects or arthropods from desired locations, such as dwelling structures, particularly in locations where food is stored. The macrocycles of the present invention can also be used to disrupt arthropod mating.

Further, the macrocycles of the present invention or combinations thereof can be used as a substantially pure substance or as a component in compositions or formulations of substances in medicinal applications, particularly as neurotoxins.

BRIEF DESCRIPTION OF THE DRAWINGS

FIG. 1B is a magnified view detailing a large and a small glandular hair. FIG. 1C shows an ant (*Crematogaster cerasi*) cleaning an antenna that has just contacted an *Epilachna borealis* pupa (left) by brushing the antenna with its foreleg (Scale bars: (B)=50 μm, (C)=1 mm).

DETAILED DESCRIPTION OF THE INVENTION

Figure 1A:
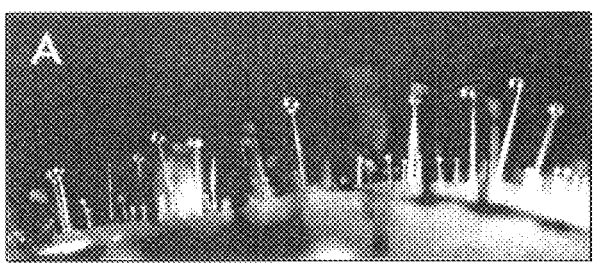
FIGS. 1A, 1B, and 1C, respectively, are scanned images of a surface of *Epilachna borealis* pupa, showing glandular hairs of two sizes (amid non-glandular bristles).
Figure 1B:
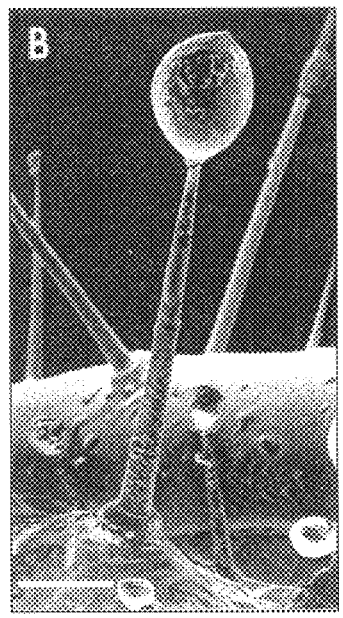

The present invention relates to macrocycles, the synthesis of these macrocycles, intermediates that are useful in synthesizing these macrocycles, and the use of these macrocycles in the management of arthropods. One aspect of the present invention relates to an isolated macrocycle having the formula:

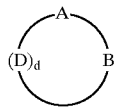

In the above formula, d is an integer from 0 to about 100 and is meant to indicate the number of D ring components, which together with the A ring component and the B ring component, constitute the macrocycle. The total number of ring components, thus can range from 2 (i.e., when d is 0) to about 102 (i.e., when d is about 100). Preferably, d is from 0 to about 30. For example, d can be 0, 1, 2, 3, 4, 5, 6, 7, 8, 9, and 10. When d is 0, $(D)_d$ represents a second bond between ring components A and B.

A, B, and each D can be the same, or they can be different. Each of these ring components can have the formula:

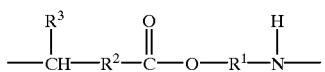

(referred to herein as the ester form) or, alternatively, it can have the formula:

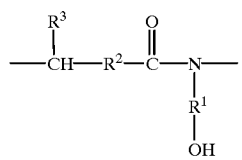

(referred to herein as the amide form). For example, when the macrocycle has 6 ring components (i.e., A, B, and 4 Ds), all of the ring components (e.g., A, B, and each D) can be in the ester form. Alternatively, two ring components (e.g., A and one of the Ds) can be in an ester form, and four ring components (e.g., B and the remaining 4 Ds) can be in an amide form. Still alternatively, one ring component (e.g., one of the Ds) can be in amide form, and five ring components (e.g., A, B, and the remaining 3 Ds) can be in the ester form.

In the formulae representing the ester and amide forms of the ring components, each $R^1$ is the same or different and is a bivalent alkylene group. That is, for example, if the macrocycle has two ring components (i.e., A and B), then, irrespective of whether both A and B are in the ester form, both A and B are in the amide form, or one is in ester form and the other in amide form, $R^1$ on the A ring component could be one kind alkylene group (e.g., a methylene) while $R^1$ on the B ring component could be another kind of alkylene (e.g., a propylene). Alternatively, the $R^1$s on A and B could be the same (e.g., they could both be an propylene groups). Each $R^2$ in the above formulae representing the ester and amide forms of the ring components is the same or different and is a bivalent alkylene group, preferably a saturated bivalent alkylene group.

Suitable alkylenes, as used in the context of $R^1$ and $R^2$, include methylene, ethylene, propylene, butylene (e.g., n-butylene), pentylene (e.g., n-pentylene), hexylene (e.g., n-hexylene), heptylene (e.g., n-heptylene), octylene (e.g., n-octylene), nonylene (e.g., n-nonylene), and the like. Preferably, $R^1$ is linear; more preferably, it is unsubstituted and has from about 1 to about 4 carbon atoms; and, most preferably, $R^1$ has the formula $—(CH_2)_n—$, where n is an integer from about 1 to about 4, preferably 2. Preferred macrocycles of the present invention are those in which each $R^1$ is the same and has the formula $—CH_2CH_2—$. $R^2$ is preferably linear; more preferably, it is unsubstituted and has from about 4 to about 10 carbon atoms; and, most preferably, $R^2$ has the formula $—(CH_2)_m—$, where m is an integer from about 4 to about 10. Preferred macrocycles of the present invention are those in which each $R^2$ is the same or different and has the formula $—(CH_2)_m—$, where m is the same or different and is an integer from about 6 to about 8. For example, the macrocycle of the present invention can contain ring components in each of which $R^2$ is the same and has the formula $—(CH_2)_7—$.

In the above formulae representing the ester and amide forms of the ring components, $R^3$ is either a hydrogen atom or an alkyl group, such as a methyl, ethyl, propyl (e.g., n-propyl), or butyl (e.g., n-butyl) group. When $R^3$ is alkyl, it is preferably a lower alkyl, for example, an alkyl containing from 1 to 6 carbon atoms. Such alkyls include moieties having the formula $—(CH_2)_r CH_3$, where r is from about 1 to about 5. Preferably, $R^3$ is saturated and unsubstituted. The various $R^3$s on the various ring components can be different, or, preferably, the same. Preferably, the $R^3$s of all ring components of the macrocycle are methyl.

As indicated above, each component of the macrocyclic ring can be in amide form. That is, A, B, and each D can be the same or different and have the formula:

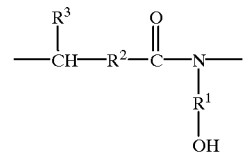

When the macrocycle having all amide ring components is to be prepared synthetically, it may be advantageous, from the standpoint of ease of starting material procurement, that each $R^2$ in the macrocycle be the same and that each $R^1$ in the macrocycle be the same. For example, each $R^2$ can be $—CH_2CH_2—$, and each $R^1$ can be $—(CH_2)_8—$.

Alternatively, each component of the macrocyclic ring can be in ester form. That is, A, B, and each D can be the same or different and have the formula:

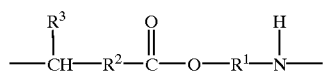

In some situations, it may be advantageous that each $R^2$ in such a macrocycle be the same and that each $R^1$ in the macrocycle be the same. For example, each $R^1$ can be —$CH_2CH_2$—, and each $R^2$ can be —$(CH_2)_8$—.

As used herein, an isolated macrocycle is one which is substantially free of one or more of the materials with which it naturally occurs. For example, applicants have discovered that macrocycles of the present invention are found in the secretions of coccinellid pupal hairs of *Epilachna borealis* (the squash beetle). These secretions also contain varying amounts of tocopherol acetates. For example, a macrocycle that is mixed with less than about 20 wt %, about 15 wt %, about 10 wt %, about 5 wt %, about 2 wt %, or about 1 wt % of tocopherol acetate, can be considered isolated for the purposes of the present invention. It is to be understood that the isolated macrocycles of the present invention are not limited to any particular method of preparation and include, for example, macrocycles which are prepared by extraction and purification from natural sources as well as those prepared by chemical synthesis. Preferably, the macrocycle is substantially pure. In this context, substantially pure means substantially free of compounds other than those that are macrocycles of the present invention. Macrocycles that are 80%, 90%, 95%, 98%, or 99% free of compounds other than other macrocycles of the present invention are to be considered "substantially pure" as used herein.

As the skilled artisan will note, when an $R^3$ group is an alkyl group, the carbon to which $R^3$ is bonded is chiral. Macrocycle, as used herein, is meant to include those macrocycles in which all chiral carbons are in the S configuration ("all-S") or in which all chiral carbons are in the R configuration ("all-R"). Accordingly, the present invention also relates to macrocycles that are substantially optically pure, for example, 80%, 90%, 95%, or 98% optically pure. Macrocycles, as used herein, also include those macrocycles in which some of the chiral carbons are in the S configuration and some are in the R configuration ("mixed R/S"). Moreover, combinations of mixed R/S, all-S, and all-R macrocycles are also intended to be included within the present application's meaning of macrocycles.

Exemplary compounds of the present invention include those having the following formulae:

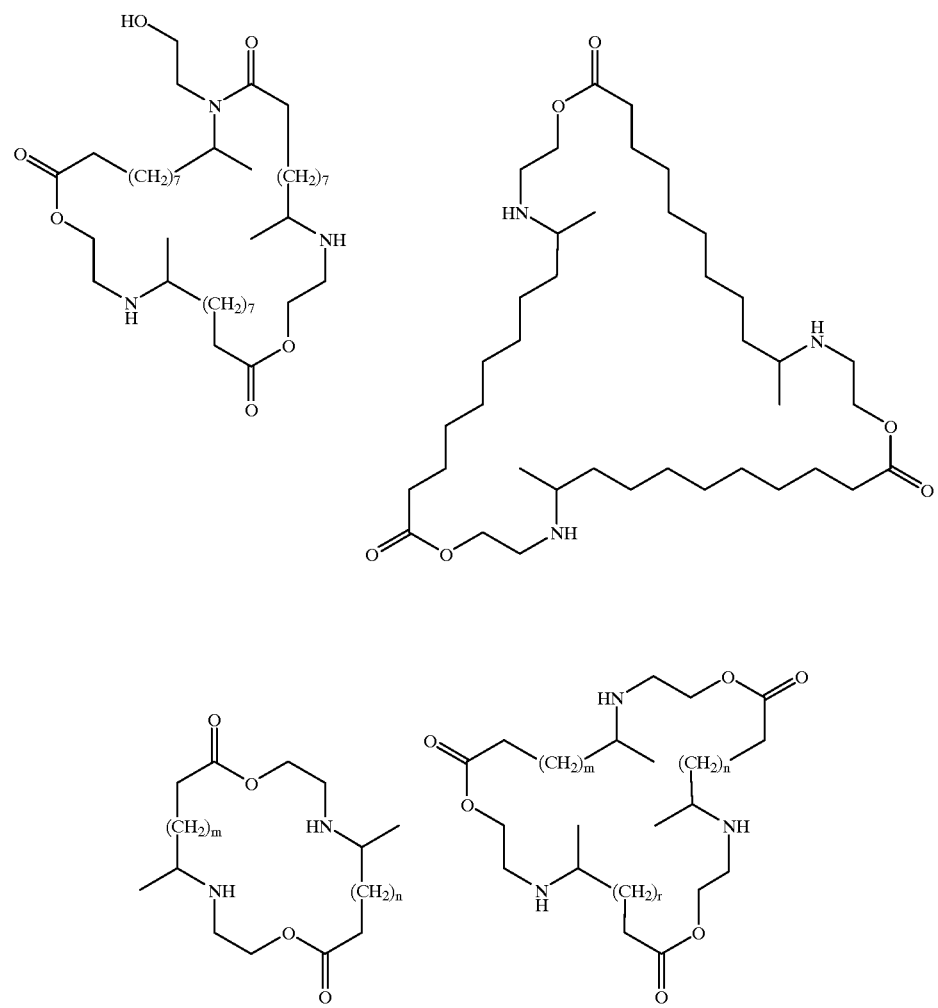

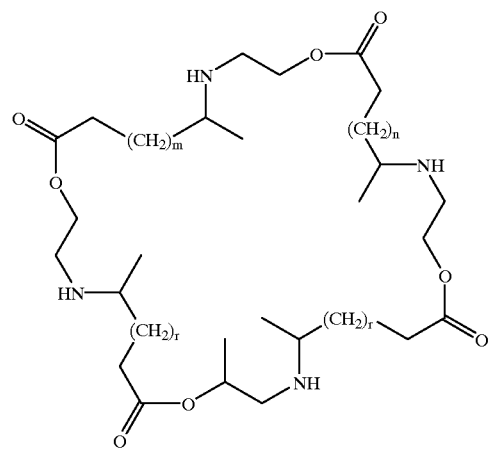
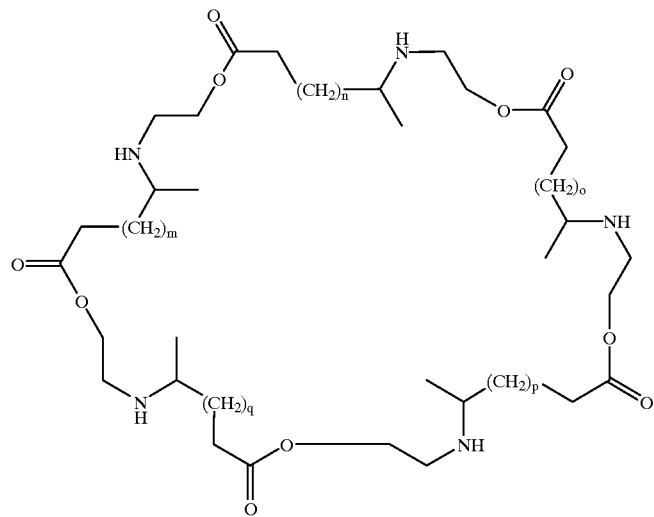
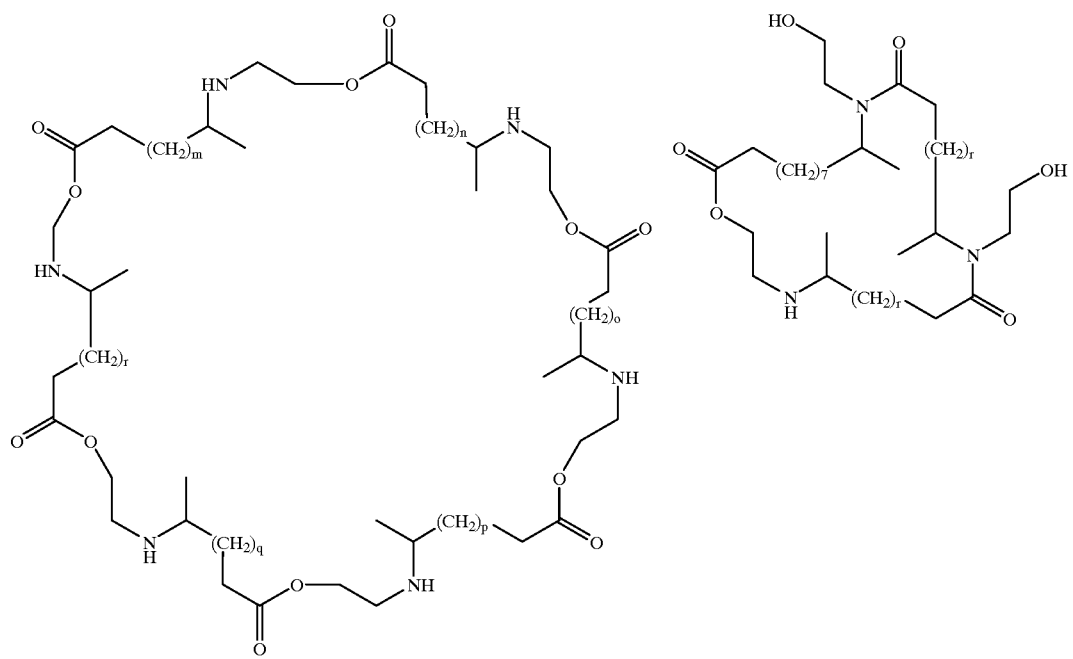

-continued

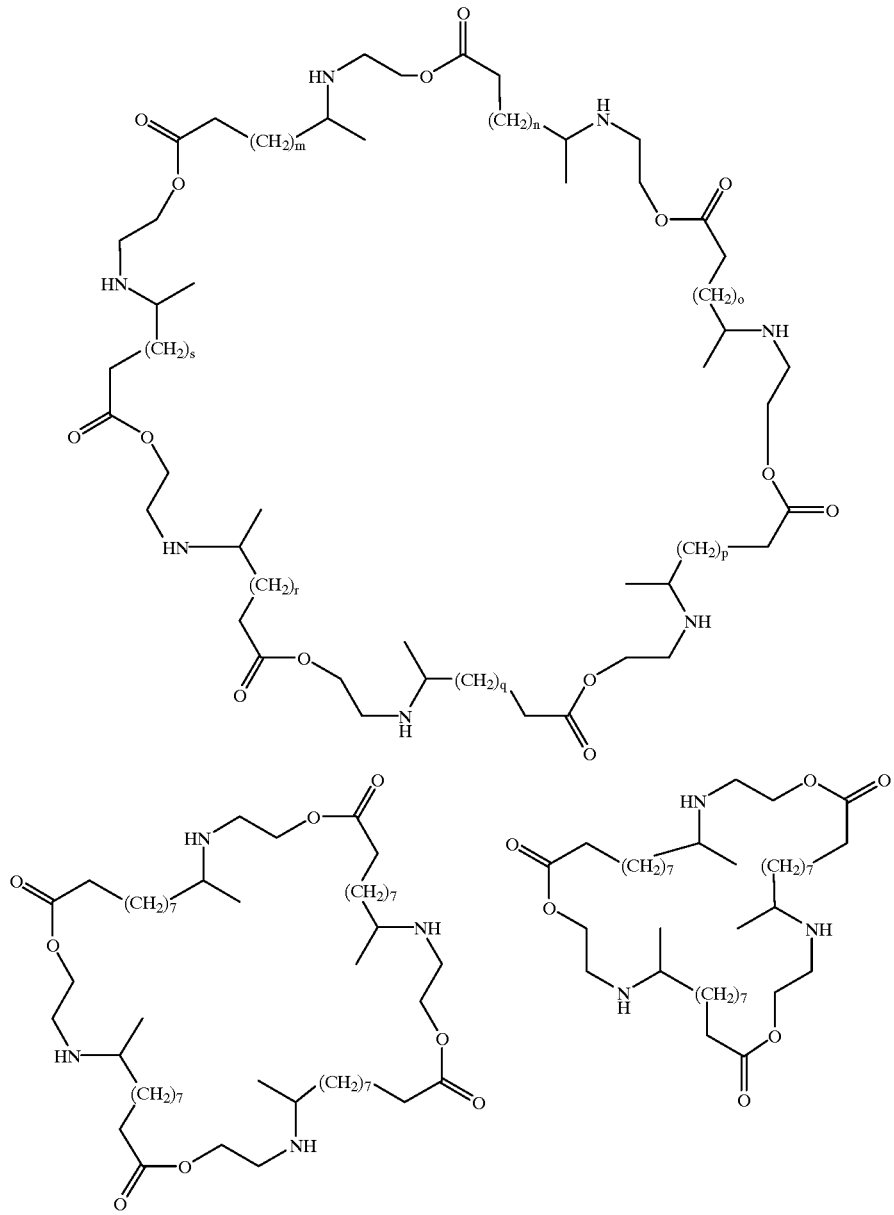

Macrocycles of the present invention in which all of the ring components (i.e., A, B, and each D) are in ester form can be prepared from an isolated linear compound having the formula:

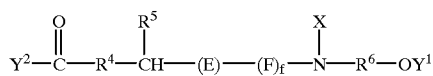

where f is from 0 to about 100 and where E and each F are the same or different and have the formula:

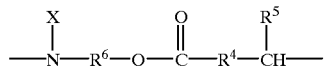

where each $R^4$ is the same or different and is a bivalent alkylene moiety; each $R^5$ is the same or different and is selected from the group consisting of a hydrogen atom and an alkyl moiety; and each $R^6$ is the same or different and is a bivalent alkylene moiety. Suitable alkylene moieties and alkyl moieties for $R^4$, $R^5$, and $R^6$ include those set forth above with regard to $R^2$, $R^3$, and $R^1$, respectively. Each X is the same or different and is a hydrogen atom or an amine protecting group, such as a t-butyloxycarbonyl ("Boc") group, a 1-adamantyloxycarbonyl ("Adoc") group, a 1-(1-adamantyl)-1-methylethyloxycarbonyl ("Adpoc") group, and a trifluoroacetyl ("TFA") group. $Y^1$ is a hydrogen atom or an alcohol protecting group. Suitable alcohol protecting groups include t-butyldimethylsilyl ("TBS") groups, t-butyldiphenylsilyl ("TBDPS") groups, triisopropylsilyl ("TIPS") groups, isopropyldimethylsilyl ("IPDMS") groups, t-hexyldimethylsilyl ("TDS") groups, and tetrahydropyranyl ("THP") groups. $Y^2$ is an OH group or a carboxylic acid protecting group, examples of which include benzyloxy, diphenylmethyloxy, 2-methylthioethoxy, and di(o-nitrophenyl)methyloxy groups.

As one skilled in the art will recognize, $R^4$, $R^5$, and $R^6$ in the E and F moieties can be selected based on the identities of $R^2$, $R^3$, and $R^1$, respectively, in each of the B and D ring components in the desired macrocycle. For example, if the desired macrocycle has a ring component B where $R^1$ is —$CH_2CH_2$—, $R^2$ is —$(CH_2)_8$—, and $R^3$ is a methyl group, an isolated linear compound suitable for use in preparing the desired macrocycle could contain an E moiety having an $R^6$ of —$CH_2CH_2$—, an $R^4$ of —$(CH_2)_8$—, and an $R^5$ of —$CH_3$. The identities of $R^4$, $R^5$, and $R^6$ that are explicitly recited in the formula for the isolated linear compound can be selected based upon the identities of $R^2$, $R^3$, and $R^1$ in the A ring component of the desired macrocycle. In addition, the value of f (i.e., the number of F moieties) in the linear compound should be the same as the value of d (i.e., the number of D moieties) in the desired macrocycle.

The macrocycle of the present invention can be prepared by cyclizing the linear compound under conditions effective to produce a macrocycle wherein each of the A, B, and D ring components is in ester form, i.e., where each of the ring components has the formula:

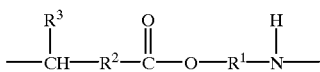

In the case where $Y^1$ is H and $Y^2$ is OH, this can be carried out simply by reacting the isolated linear compound under conventional ester formation conditions. For example, the reaction can be carried out in a suitable solvent, such as acetonitrile, a ketone solvent (e.g., acetone, methyl ethyl ketone, or cyclohexanone), a hydrocarbon solvent (e.g., hexanes and octane), or an aromatic solvent (e.g., toluene and benzene). The preferred solvent is acetonitrile. Preferably, the solvent is dry, and, more preferably, the reaction is carried out using an apparatus or in the presence of a material or apparatus which removes, from the reaction mixture, the water produced in the course of the reaction. For example, water can be removed by using a still head equipped with a Clasien trap or by contacting the mixture with a suitable salt, preferably Mukaiyama salt (i.e., 2-chloro-N-methylpyridinium iodide), which is capable of tying up the water produced by the condensation reaction. The reaction can be carried out at a temperature of from room temperature to the boiling point of the solvent, preferably at the boiling point of the solvent, for from 10 minutes to 2 days, preferably from about 1 hour to about 8 hours, more preferably from about 3 hours to about 5 hours.

In the case where $Y^1$ is an alcohol protecting group, it can be removed, using conventional methods, prior to carrying out the above cyclization reaction. For example, the linear compound bearing an alcohol protecting group which is a silyl ether can be reacted with a molar excess, preferably only a slight molar excess, of tetra butylammonium fluoride ("TBAF") preferably provided as a concentrated aqueous solution (e.g., from about 0.1 M to just below saturation) without the use of additional solvents. The reaction is generally carried out at from about 10° C. to about 40° C., preferably at about room temperature, for from about 1 hour to about 5 days, preferably from about 12 hours to about 24 hours.

In the case where $Y^2$ is carboxylic acid protecting group, it can be removed, using conventional methods, prior to the above-described cyclization. For example, in the case where $Y^2$ represents an arylmethyloxy group (e.g., a benzyloxy group), it is most conveniently removed by hydrogenation, preferably over a catalyst such as a Pd/C catalyst, for from 1 hour to 4 days, preferably for from about 1 day to about 2 days. The hydrogenation reaction is advantageously carried out in an alcoholic solvent (e.g., methanol, ethanol, and i-propanol) at a concentration of from about 0.01 moles to about 1 mole of carboxylic acid protected linear compound per liter of solvent.

As indicated above the one or more of the amines in the above linear compound can be present in protected form. These can be deprotected prior to or, preferably, subsequent to cyclization by treatment with trifluoroacetic acid ("TFA") or similar deprotecting agent. Generally, this reaction is carried out at a concentration of about 0.01 to about 1 mole of a substantially pure amine protected macrocycle or linear compound per liter of deprotecting agent. The amount of deprotecting agent used will, of course, vary depending on the number of protected amines present in the macrocycle or linear compound.

The linear compound that is the starting material for the above-described cyclization process can be prepared by reacting linear monomers having the formula:

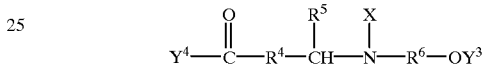

under conditions effective to produce the isolated linear compound. In the above formula for the linear monomers, each $R^4$ is the same or different and is a bivalent alkylene moiety. That is, some of the monomers can contain one type of $R^4$ moiety (e.g., —$CH_2CH_2$—) while others may contain different $R^4$ moieties (e.g., —$CH_2CH_2CH_2$—) or, alternatively, all monomers can contain the same $R^4$ moieties (e.g., all linear monomers can contain —$CH_2CH_2$— moieties). The $R^6$ moieties in the linear monomers can be the same or different. They are bivalent alkylenes, such as saturated alkylenes having, for example, the formula —$(CH_2)_c$— where c is from about 4 to about 10 (e.g. —$(CH_2)_8$— and —$(CH_2)_7$—) and unsaturated alkylenes having, for example, the formula —$(CH_2)_g$—(CH=CH)—$(CH_2)_h$—, where g+h is from about 2 to about 8 and each of g and h is at least 1. X, $Y^3$, and $Y^4$ in each of the monomers can be the same or different, and are defined, respectively, as above with regard to X, $Y^1$, and $Y^2$.

The linear monomers are preferably reacted in a controlled and sequential manner to produce the linear compound.

For example, a linear monomer having the formula:

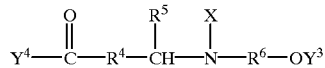

where $Y^3$ is H and $Y^4$ is OH, can be protected at the carboxyl group by reacting it with a suitable protecting agent, such an alcohol (e.g., benzyl alcohol, diphenylmethanol, 2-methylthioethanol, and di-(o-nitrophenyl)methanol) under conditions effective to esterify the carboxylic acid functionality on the linear monomer. This reaction is advantageously carried out in an inert solvent, such as chlorinated hydrocarbons (e.g., chloroform, dichloromethane, and tetrachloroethylene), hydrocarbon solvents (e.g., hexanes and octane), ketone solvents (e.g., acetone, methyl ethyl ketone, and cyclohexanone), and aromatic hydrocarbon solvents (e.g., toluene and benzene). Preferably, the reaction is carried out in the presence of a base, such as 4-dimethylaminopyridine ("DMAP"), pyridine, and triethylamine, and a coupling agent, such as dicyclohexylcarbodiimide ("DCC") (each in a molar excess, preferably in a slight molar excess), for from about 1 hour to about 4 days, preferably from about 12 hours to about 20 hours, and at a temperature from about 20° C. to about the solvent reflux temperature, preferably at about room temperature.

In a separate reaction, a linear monomer having the above formula, where $Y^3$ is H and $Y^4$ is OH, can be protected at the hydroxyl functionality by reacting it with a suitable protecting agent, such as a silylating agent or dihydropyrane. Suitable silyl protecting agents include silylating agents bearing three alkyl or aryl substituents, especially those containing at least some bulky alkyl substituents. Examples of suitable silylating agents include t-butyldimethylsilyl, t-butyldiphenylsilyl, isopropyldimethylsilyl, and t-hexyldimethylsilyl chlorides and trifluorosulfonate. Alternatively, linear monomers having a protected alcohol functionality can be prepared by reacting a reactive amine compound having the formula $Y^4$—C(O)—$R^4$—CH($R^5$)—NH—X with an alkylating agent containing a protected alcohol, for example, having the formula Q—$R^6$—$OY^3$, where Q is a leaving group (e.g., a halogen atom, for example, bromine), $Y^3$ is an alcohol protecting group, and $R^6$ is as set forth above with respect to the description of linear monomers. The reaction is preferably carried out below room temperature (0° C. being typical) with equimolar amounts of the reactive amine compound and alkylating agent and with stirring for from about 1 day to about 1 week. Preferably, prior to adding the alkylating agent, the amine's hydrogen is abstracted with a suitably strong base, such as sodium hydride (NaH).

Still alternatively, the hydroxyl functionality on the linear monomer can be introduced earlier during the synthesis of the linear monomer, as described in greater detail below.

Once the linear monomer having a protected carboxylic acid group and an unprotected alcohol group and the linear monomer having an unprotected carboxylic acid group and a protected hydroxy group are prepared, they are contacted with each other under conditions effective to react the unprotected carboxylic acid functionality of the one monomer with the unprotected hydroxy functionality of the other monomer. This reaction can be carried out by stirring the reactants for from about 1 hour to about 12 hours, preferably from about 2 hours to about 6 hours, in a suitable solvent (such as those specified above with regard to esterifying the linear monomer's carboxylic acid functionality) preferably in the presence of an excess, more preferably a slight excess, of DCC and DMAP.

If the dimer is the desired form of the linear compound (i.e. if f in the formula for the linear compound is 0), then the reaction product of these 2 monomers can be cyclized as set forth above to produce a macrocycle of the present invention containing two ring components A and B.

If, instead, a macrocycle having three or more ring components is desired, then a trimeric linear compound is needed. This can be produced by deprotecting the alcohol function of the above-prepared dimeric linear compound and reacting this deprotected dimer with an appropriate linear monomer having an unprotected carboxylic acid functionality. Suitable reaction conditions include those set forth above with regard to formation of the dimer. Alternatively, the extension of the dimeric linear compound to the trimeric linear compound can be carried out by deprotecting the carboxylic acid function of the above-prepared dimeric linear compound and reacting this deprotected dimer with an appropriate linear monomer having an unprotected alcohol functionality.

The resulting trimer can be cyclized, as described above, to form a three-component macrocycle (i.e., one having A, B, and one D). Alternatively, the trimer can be deprotected at either its hydroxy or carboxylic acid functionality and then further reacted with a suitably deprotected and substituted monomer to form the tetramer. It is also envisioned that, in some situations, the tetramer can be advantageously prepared by separately deprotecting the carboxylic acid function on a portion of the dimer sample and deprotecting the alcohol function on another portion of the dimer sample. The carboxylic acid deprotected dimer is then reacted with the alcohol deprotected dimer under suitable reaction conditions (e.g., those that were used to prepare the dimer) to produce the tetrameric linear compound.

The tetramer can be cyclized as described above, or the process of deprotecting the linear compound and reacting it with monomer to increase the number of components therein by one can be repeated as many times as is necessary to produce an n-mer linear compound, where n is the number of ring components present in the desired macrocycle. Alternatively, convergent synthetic strategies can be employed.

As noted above, the $R^4$ moieties in one or more of the linear monomers may, optionally, be unsaturated. This unsaturation can be removed at any step during the above-described process. However, it is preferred to maintain the unsaturation, if any, in the n-mer until the desired linear compound has been constructed. At that point, all unsaturation can be removed at once by hydrogenating the linear compound, preferably in an alcoholic solvent over a catalyst, such as Pd/C. Generally, if this methodology is followed, deprotection of the linear compound's carboxylic acid group that is performed immediately prior to cyclization can be effected simultaneously with the hydrogenation of any unsaturation that may be present in the linear compound.

Deprotection of the amine groups can be effected, preferably after cyclization, by treating the protected amine groups with neat trifluoroacetic acid, as described above.

Once the macrocycle of the present invention containing only ring components in the ester form has been prepared, one or more of the ring-components in ester form can be converted to its amide form. This can be carried out by treating the macrocycle having all ring components (i.e., A, B, and each D) in ester form under conditions effective to cause at least one O-to-N acyl transfer. The O-to-N acyl transfer is most readily effected by permitting the macrocycle to stand at room temperature for a period of time ranging from 15 minutes to 3 months. Alternatively, the O-to-N acyl transfer can be promoted by heating the macrocycle or by treating it with organic bases, such as DMAP, pyridine, and triethylamine, in a suitable organic solvent, such as a hydrocarbon or ether solvent. In cases where it is desired that O-to-N acyl transfer be prevented, the macrocycles of the present invention can be stored at reduced temperature (e.g., under liquid nitrogen) or in an acidic form (e.g., produced by reacting the macrocycle with an acid under conditions effective to protonate at least some (preferably most or all) of the macrocycles' amine nitrogens).

The macrocycles of the present invention can be used to repel various arthropods, especially insects (e.g., ants, termites, and cockroaches), and spiders. To repel arthropods, the macrocycles of the present invention can be used alone. Alternatively, they can be used in a composition containing another macrocycle of the present invention (i.e., containing a macrocycle of the present invention that has a different formula). For example, one of the macrocycles in the composition can have three ring components, while the other can have five ring components. Alternatively, both macrocycles can have 5 ring components, but, in one, all of the ring components can be in the ester form while, in the other, at least some of the ring components can be in amide form. Still alternatively, the two macrocycles can have the same number of ring components all of which are in the same form, but the first macrocycle's $R^1$, $R^2$, and $R^3$ moieties can be different than those of the second macrocycle. In any of the above compositions, the proportions of the various macrocycles in the composition is not critical to the practice of the present invention. Preferred compositions of the present invention are those which contain about 0–5 molar %, more preferably about 0–2 molar % of dimers (i.e., macrocycles having d=0), about 35–55 mole %, more preferably from about 44–50 mole % of trimers (i.e., macrocycles having d=1), about 25–45 mole %, more preferably about 34–40 mole % of tetramers (i.e., macrocycles having d=2), about 4–18 mole %, more preferably about 8–14 mole % of pentamers (i.e., macrocycles having d=3), about 0–8 mole %, more preferably about 1–5 mole % of hexamers (i.e., macrocycles having d=4), and about 0–5 mole %, preferably about 0–2 molar % of heptamers (i.e., macrocycles having d=5).

Whether the arthropod repellent contains a single macrocycle or a combination of two or more macrocycles, the arthropod repellent can also include a carrier. The type of carrier to be employed depends on the use to which the repellent is to be put. For example, where the arthropod repellent is to be used on human skin, suitable carriers include mono- and di-glycerides, fatty alcohols (e.g., stearyl alcohol), and esters of fatty alcohols. Where the arthropod repellent is to be used on plants, carriers, such as vegetable oils, refined mineral oils, rubbers, plastics, silica, diatomaceous earth, and cellulose powder can be employed. In either case, the arthropod repellent can be provided in the form of a solution, a dispersion, a spray, such as an emulsifiable concentrate or a wettable powder, an aerosol, a dust, a granular formulation, and a laminated slow release formulation. Still alternatively, the arthropod repellent can be placed on a support to repel insects or other arthropods from a location proximate to the support. Suitable supports include, for example, picnic tables, benches, drinking fountains, lavatory fixtures (e.g., the underside of wall hung sinks), pet cages, pet collars, and blocks of wood or plastic whose sole function is to act as a support for the repellent.

The arthropod repellents of the present invention can also contain, in addition to the macrocycle or combination of macrocycles of the present invention, an acidic stabilizer, preferably from about 1 to about 30 equivalents of an organic acid (e.g., acetic acid), an inorganic acid (e.g., hydrochloric acid or sulfuric acid), or an acidic buffer system (e.g., an acidic phosphate buffer system). Additionally or alternatively, the repellent of the present invention can include one or more antioxidants. Suitable antioxidants include tocopherols, such as Vitamin E, tocopherol acetates, such as Vitamin E acetate and alpha-tocopherol acetate, and ascorbic acid.

The macrocycle of the present invention is generally used to repel arthropods from various surfaces by disposing the macrocycle on such surfaces. Examples of surfaces include a surface of an animal, such as a dog, a cat, a farm mammal (e.g., a rabbit, a horse, a cow, a pig, a sheep, and a goat), a zoo animal, and a human. Other surfaces from which arthropod repellency may be desired include those of a plant (such as a leaf surface, a stem surface, a root surface, a flower surface, and a fruit surface) and a surface of a fruit or vegetable that has been harvested from a plant. Other surfaces, such as the surfaces of structures where insects or other arthropods nest or live, for example, in wall cavities, floor cavities, cabinets, drawers, storage containers, rugs, upholstery, and carpeting, can be made to repel arthropods by applying the macrocycles of the present invention thereto. The repellent of the present invention can be applied in inaccessible areas to drive insects or other arthropods from these areas so that they can be killed with pesticides at a location where their bodies would be accessible. This can be especially advantageous, because many people have adverse reactions to the allergens emitted by insect bodies left in inaccessible areas. The arthropod repellents of the present invention are envisioned as having particular utility in repelling arthropods, particularly insects (e.g., ants, termites, and cockroaches), from stored foods and locations where foods are stored (e.g., containers in which foods are kept). Irrespective of the surface onto which it is to be applied, such application can be carried out by any suitable method, including painting, rolling, brushing, spraying, dipping, and the like.

The macrocycles of the present invention can also be used to disrupt arthropod (e.g., insect) mating by applying the macrocycle to the arthropods thus making them repulsive to one another. This can be done by broadcasting the macrocycle into an area known to contain a population of such arthropods. Alternatively, the arthropods can be attracted to a particular location using an appropriate attractant, such as a pheromone. Once the arthropods are at the particular location, they can be contacted with the macrocycle of the present invention, preferably in a form that permits the macrocycle to adhere to the arthropods, such as in an oil.

The macrocycles of the present invention may also be utilized in medicinal applications, such as ion-channel inhibitors. As observed, the macrocycles include two structural characteristics. First, the macrocycle compounds are lipophilic (non-polar) alkaloids. Second, the macrocycle compounds are also cyclic oligo-esters and/or oligo-amides, thereby resembling cyclic peptides. Both lipophilic alkaloids and cyclic peptides are utilized as neurotoxins in medicinal applications, particularly for their potent biological activities related to neurobiological or signal-transduction mechanisms.

Lipophilic alkaloids have been isolated from animal sources and found to be effective in applications involving neurological sodium channels. For example, batrachotoxin is one of a large group of alkaloids that have been isolated from frogs and found to be effective in various neurological applications, batrachotoxin, for example, represents one of the potent neurotoxins acting on the inactivation of voltage-gated sodium channels. Further discussion on the relationship between sodium channel activity and batrachotoxin is found in the following articles: Habermehl, G. G., "Neurotoxins from Amphibians", *Toxicon,* 29: 1165–1166 (1991), Benoit, Evelyne, "Mechanism(s) of Action of Neurotoxins Acting on the Inactivation of Voltage-Gated Sodium Channels", *Comptes Rendus des Seances De la Societe de Biologie et de ses Filiales,* 192 (3): 409–436 (1998), Brown, George B., "Insights on the Voltage-Sensitive Sodium Channel: The Batrachotoxin Connection", Toxicon, 27: 21–22 (1989), and Gavsovsky, Fabian, et al., "Interaction of Pumiliotocin B with an 'Alkaloid-Binding Domain' on the Voltage-Dependent Sodium Channel", *Molecular Pharmacology,* 42 (6): 1104–1108 (1992), all of said articles incorporated herein by reference. Relatedly, Tang, L., et al., "Effects of Besipirdine at the Voltage-Dependent Sodium Channel", *British Journal of Pharmacology,* 116 (5):

2468–2472 (1995), incorporated herein by reference, indicate that besipirdine, also a lipophilic alkaloid, inhibits voltage-dependent sodium and potassium channels and binds to these channels in a similar fashion as batrachotoxin. Indications are that besipirdine may be useful in the treatment of Alzheimer's disease.

Cyclic peptides comprising 10–30 amino acid residues likewise have been isolated from several different groups of animals and have been found to have physiological and pharmacological impact on both vertebrate and invertebrate nervous systems. One example of a polypeptide toxin comprises the conotoxins isolated from cone snails, as disclosed by Myers, Richard A, et al., "Conus Peptides as Chemical Probes for Receptors and Ion Channels", *Chem. Rev.*, 93:1923–1936 (1993), incorporated herein by reference.

Due to the structural characteristics of the macrocycles of the present invention as discussed above, it is concluded that these macrocycles likewise have physiological and pharmacological impact on the nervous systems of both vertebrate and invertebrate animals, particularly when utilized as a neurotoxin. These macrocycles may be utilized in amounts and under conditions effective to act as a neurotoxin in both vertebrate and invertebrate animals.

The macrocycle compounds herein may be made up in any suitable form appropriate for the desired use; e.g., oral, parenteral (for example, subcutaneously, intravenously, intramuscularly, intraperitoneally, by intranasal instillation, or by application to mucous membranes, such as that of the nose, throat, and bronchial tubes, or by instillation into hollow organ walls or newly vascularized blood vessels) or topical administration. Suitable dosage forms for oral use include tablets, dispersible powders, granules, capsules, suspensions, syrups, and elixirs. The compounds may be administered alone or with suitable pharmaceutical diluents or carriers.

It will be appreciated that the actual preferred amount of the macrocycle compound to be administered according to the present invention will vary according to the particular compound, the particular composition formulated, and the mode of administration. Many factors that may modify the action of the compound can be taken into account by those skilled in the art; e.g., body weight, diet, time of administration, route of administration, rate of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests.

The present invention is further illustrated by the following examples.

EXAMPLES

Example 1

Preparative Scheme for the Synthesis of PAML-681

The following reaction scheme summarizes the synthetic procedure employed to prepare the PAML-681.

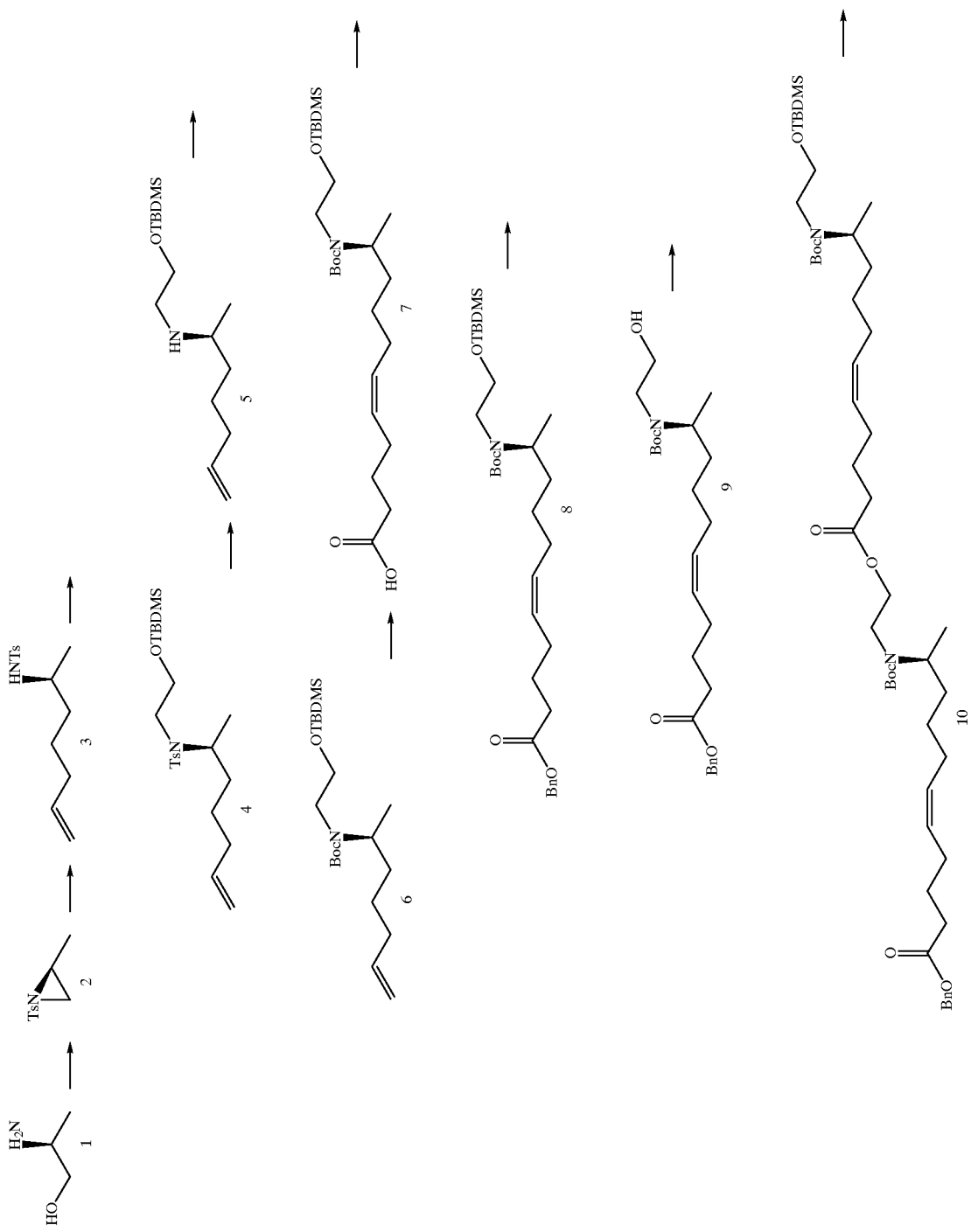

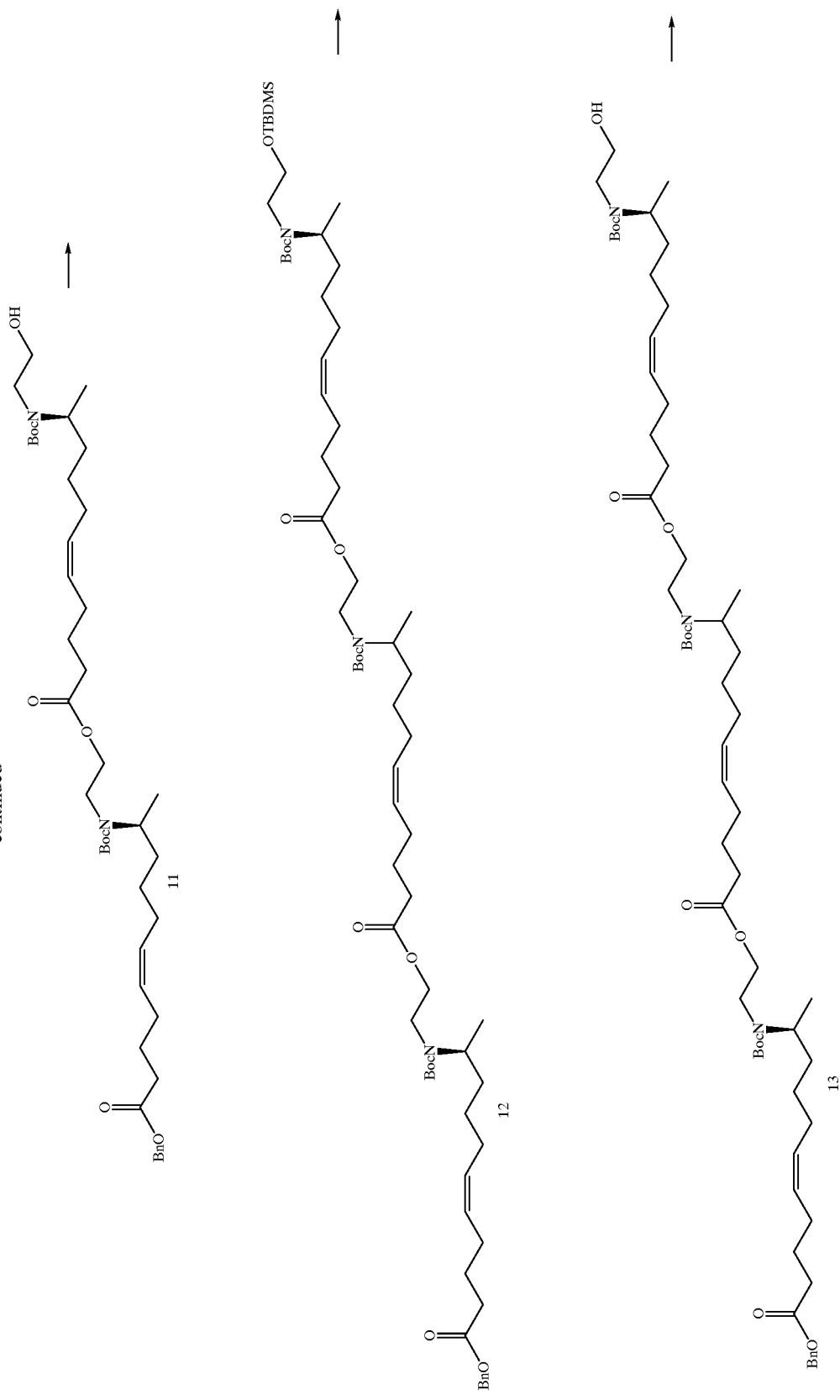

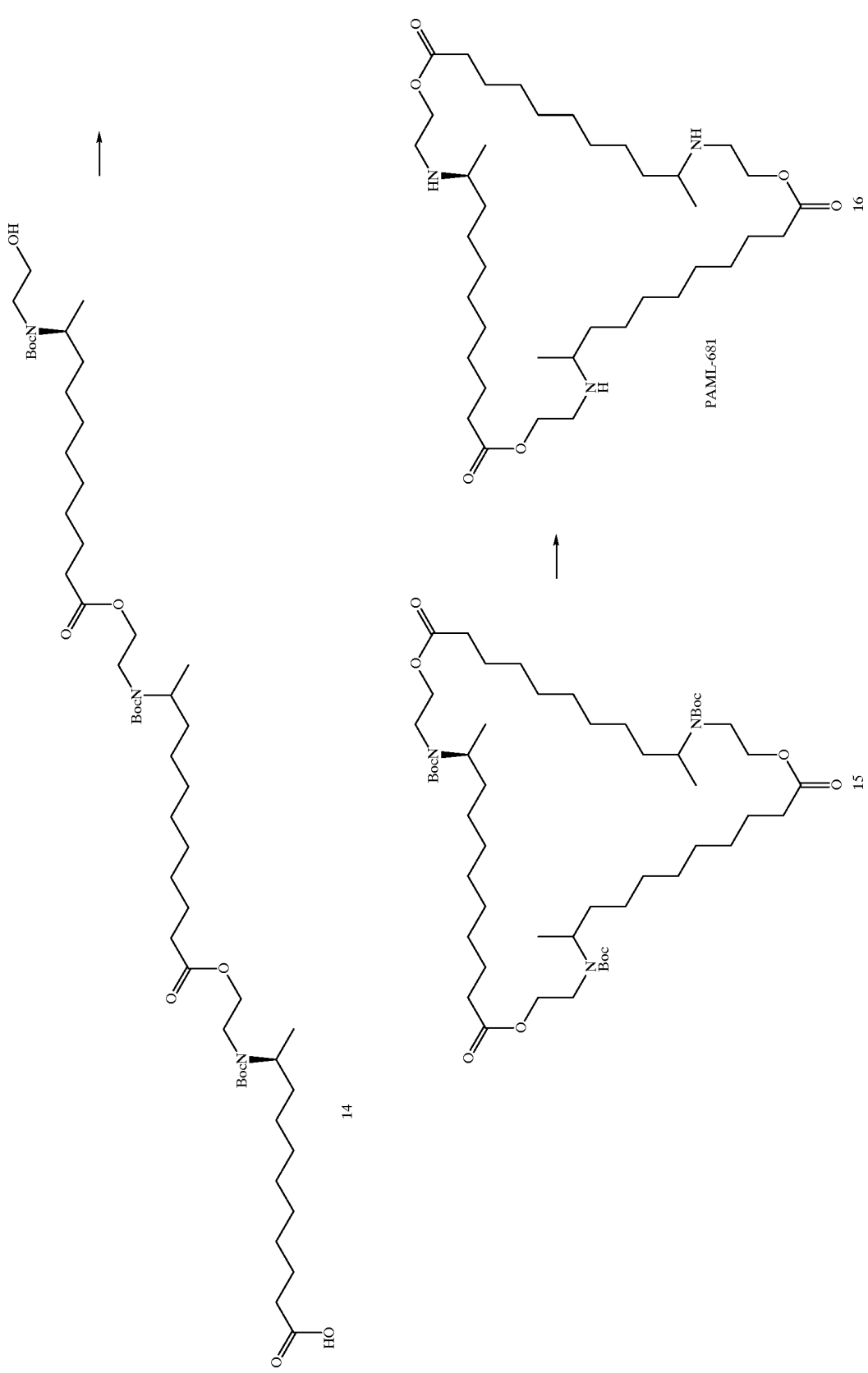

Example 2

Preparation of S-(+)-2-methyl-N-p-tosylaziridine (2)

A 50 mL pear-shaped flask was charged with a mixture of tosyl chloride (4.19 g, 22 mmol), pyridine (3.5 mL) and dichloromethane (6.5 mL). The mixture was cooled to 0° C., and S-(−)-2-amino-1-propanol (1) (0.751 g, 10.0 mmol) was added dropwise. The mixture was allowed to warm to rt. and stirred for 16 h. The reaction mixture was then poured into a separatory funnel containing 50 mL of cold 1N HCl and 25 mL $CH_2Cl_2$. After extraction, the organic layer was separated and washed with saturated aqueous $CuSO_4$ (1×25 mL) and saturated aqueous NaCl (1×25 mL). Each aqueous layer was back-extracted with $CH_2Cl_2$ (2×25 mL). The organic fractions were combined, dried ($MgSO_4$), and concentrated in vacuo to give 3.9 g of a greenish oil which was taken up in 50 mL dry acetone and stirred over 5.0 g of $K_2CO_3$ for 14 h. This mixture was then filtered through Celite and concentrated in vacuo to give 3.4 g of a yellow oil. The yellow oil was purified by flash chromatography (50 mm×6" column, eluted with 18% v/v EtOAc/hexane) to give 1.99 g of a white solid which was further purified by recrystallization from refluxing petroleum ether to give 1.86 g (8.8 mmol, 88% yield) of the title compound (2) as colorless needles (m.p. 57–58°) $[\alpha]_D^{25}$=+32.0° (MeOH, c=2.8), $^1$H NMR (500 MHz, $C_6D_6$): δ7.86–7.89 (m, 2H), 6.72–6.76 (m, 2H), 2.61 (ddq, J=6.9, 4.4, 5.6 Hz, 1H, C$\underline{H}$CH$_3$), 1.84 (s, 3H, ArC$\underline{H}_3$), 2.34 (d, J=6.9 Hz, 1H, C$\underline{H}_a$H$_b$CHNTs) 1.37(d, J=4.5 Hz, 1H, CH$_a\underline{H}_b$CHNTs), 0.76 (d, J=5.6 Hz, 3H, C$\underline{H}_3$).

Example 3

Preparation of S-(−)-6-p-toluenesulfonylamino-1-heptene (3)

Di-3-butenylmagnesium was prepared as follows. A three-neck 100 mL round-bottom flask, outfitted with a reflux condenser, septum inlet, and Schlenk-type fritted tube (the end of which was attached to a second three-neck flask equipped with a septum and gas bubbler), was charged with magnesium (0.98 g, 40 mmol) and 30 mL of dry ether. After activation of the magnesium with a small amount of $I_2$ and with vigorous stirring, 4-bromo-1-butene (3.0 mL, 30 mmol) was added via syringe pump over the course of 25 minutes. After an additional 15 minutes of stirring, 1,4-dioxane (3.0 mL, 35 mmol) was added dropwise, resulting in a strong exothermic reaction and formation of a thick white precipitate. After addition of the dioxane was complete, the mixture was stirred for 30 minutes. The apparatus was then tilted allowing the reaction mixture to flow into the Schlenk tube; 5 psi argon pressure was applied forcing the solution through the frit into the second flask to yield a clear, slightly brown solution. The reaction flask and solids were rinsed with an additional 15 mL of ether, and the ether was combined with the original filtrate.

The aziridine (2) prepared in Example 1 was then alkylated as follows. A 250 mL round-bottom flask, outfitted with a septum inlet and thermocouple, was charged with CuI (6.0 mmol, 1.13 g) and 50 mL of ether, the stirred slurry was cooled to −70° C., and all of the above alkylmagnesium solution was added slowly by syringe. The cooling bath was then removed, and the solution allowed to warm slowly. At −25° C., the color of the reaction mixture changed from tan to deep orange, whence the cooling bath was replaced. When the temperature again reached −70° C., the aziridine (2) was added as its ether solution (1.8 g, 8.5 mmol in 10 mL) in one portion. The mixture was allowed to warm slowly to room temperature ("rt") and then stirred for an additional 4 h, after which it was quenched by the careful addition of 100 mL of a 4:1 v/v mixture of saturated aqueous $NH_4Cl$ and saturated aqueous $NH_4OH$. This mixture was stirred vigorously under air for 2 h, the organic layer was then separated, and the aqueous phase was extracted with ether (4×50 mL). The combined organic fractions were dried ($MgSO_4$), filtered, and concentrated in vacuo to afford a clear, colorless oil (2.8 g). This oil was purified by flash chromatography (25 mm×6" column, eluted with 20% v/v EtOAc/hexane) to give 2.14 g of the title compound (3) as a colorless oil (8.0 mmol, 94% yield). $[\alpha]_D^{25}$=−16.4° (c=3.6, MeOH), $^1$H NMR (500 MHz $C_6D_6$): δ7.89–8.00 (m, 2H), 6.85–6.92 (m, 2H), 5.62 (ddt, J=12.8, 8.4, 6.4 Hz, 1H, C$\underline{H}$=CH$_2$), 5.55 (d, J=8.1 Hz, 1H, N$\underline{H}$Ts), 4.90–4.93 (m, 1H CH=C$\underline{H}_a$H$_b$), 4.89 (t, J=2.8 Hz, 1H CH=CH$_a\underline{H}_b$), 3.28 (sept. J=6.9 Hz, 1H, C$\underline{H}$NHTs), 1.93 (s, 3H ArC$\underline{H}_3$), 1.76–1.81 (m, 2H, C$\underline{H}_2$CH=CH$_2$), 1.1–1.35 (m, 4H, (C$\underline{H}_2$)$_2$), 0.84 (d, J=7.0 Hz, 3H, C$\underline{H}_3$).

Example 4

Preparation of S-(+)-N-p-toluenesulfonyl-6-[2-tert-butyldimethylsilyloxyethylamino]-1-heptene (4)

S-(−)-6-p-toluenesulfonylamino-1-heptene (4) (2.0 g, 7.5 mmol) was added to a stirred slurry of NaH (215 mg, 9.0 mmol, in 40 mL of dry DMF) at 0° C. by syringe pump over a period of 1 h. The mixture was stirred for an additional 30 min at 0° C., and, then, 2.14 g (9.0 mmol) of (2-bromoethoxy)-tert-butyldimethylsilane was added dropwise. The mixture was allowed to warm to rt, and stirring was continued for 80 h. 40 mL of $H_2O$ was added, and the reaction mixture was extracted with a 10% v/v mixture of ether/pentane (5×50 mL). The combined organic extracts were dried ($K_2CO_3$), filtered, and concentrated to give 3.1 g of a slightly yellow oil. The yellow oil was purified by flash chromatography (25 mm×6" column, eluted with 8% v/v EtOAc/hexane) to give 2.8 g of the title compound (4) as a clear, colorless oil (6.7 mmol, 89% yield). $[\alpha]_D^{25}$=+14.3° (c=2.2, MeOH), $^1$H NMR (500 MHz $C_6D_6$): δ7.75–7.72 (m, 2H), 6.79–6.75 (m, 2H), 5.68 (ddt, J=17.1, 10.1, 6.7 Hz, 1H, C$\underline{H}$=CH$_a$H$_b$), 4.98 (dq, J=17.0, 1.7 Hz, 1H CH=C$\underline{H}_a$H$_b$), 4.96 (ddt, J=10.1, 2.2, 1.2 Hz, 1H CH=CH$_a\underline{H}_b$), 4.09 (td, J=9.6, 5.6 Hz, 1H OC$\underline{H}_a$H$_b$CH$_a$H$_b$N), 3.91 (td, J=9.4, 5.7 Hz, 1H, OCH$_a\underline{H}_b$CH$_a$H$_b$N), 3.89 (sext, J=6.7 Hz, 1H, NC$\underline{H}$CH$_3$), 3.28 (ddd, J=14.8, 9.3, 5.6 Hz, 1H, OCH$_a$H$_b$C$\underline{H}_a$H$_b$N), 3.12 (ddd, J=14.8, 9.3, 5.7 Hz, 1H, OCH$_a$H$_b$CH$_a\underline{H}_b$N), 1.94–1.89 (m, 2H, C$\underline{H}_2$CH=CH$_2$), 1.89 (s, 3H, ArC$\underline{H}_3$), 1.32–1.18 (m, 3H, C$\underline{H}_2$CH$_2$CH=CH$_2$ and C$\underline{H}_a$H$_b$CH$_2$CH$_2$CH=CH$_2$), 1.10–1.02 (m, 1H, CH$_a\underline{H}_b$CH$_2$CH$_2$CH=CH$_2$), 0.99 (s, 9H, (C$\underline{H}_3$)$_3$CSi), 0.69 (d, J=6.7 Hz, 3H, NCHC$\underline{H}_3$), 0.132 (s, 3H, (C$\underline{H}_3$)$_a$Si), 0.124 (s, 3H, (CH$_3$)$_b$Si).

Example 5

Preparation of S-(+)-O-6-[2-tert-butyldimethylsilyloxyethylamino]-1-heptene (5)

A solution of sodium naphthalide was prepared as follows. To a stirred solution of naphthalene (3.8 g, 30 mmol) in 30 ml of dry DME was added an excess of sodium metal (1.3 g, 59 mmol). This mixture was stirred vigorously for 3 hours at rt. prior to use.

The tosylate was deprotected as follows. The sulfonamide (4) (2.5 g, 5.9 mmol) was taken up in 50 mL of dry DME and cooled to −70° C. The above naphthalide solution was then added dropwise with vigorous stirring. Addition was continued until a persistent green color was achieved (12 mL). The reaction was allowed to warm to rt. and was then quenched by the addition of 5 mL of EtOH. The reaction mixture was concentrated by rotary evaporation at reduced pressure to give a solid white residue, which was taken up in 30 mL of $H_2O$ and extracted with ether (4×25 mL). The combined organic extracts were rinsed with saturated aqueous NaCl (1×25 mL), dried ($Na_2SO_4$), filtered, and concentrated to yield 4.2 g of an oily white solid which was purified by flash chromatography (25 mm×6" column, eluted with 5% v/v EtOac/hexane followed by 20% EtOac/Hexane containing 2% $Et_3N$) to give 1.46 g of the title compound (5) as a slightly yellow oil (5.6 mmol, 96% yield). $[\alpha]_D^{25}=+3.5°$ (c=3.6, $CH_2Cl_2$), $^1H$ NMR (500 MHz $C_6D_6$): δ5.78 (ddt, J=17.1, 10.1, 6.7 Hz, 1H, C$\underline{H}$=$CH_2$), 5.04 (dq, J=17.1, 1.7 Hz, 1H, CH=C$\underline{H}_aH_b$), 4.99 (ddt, J=10.1, 2.3, 1.2 Hz, 1H, CH=$CH_a\underline{H}_b$), 3.65 (t, J=5.4 Hz, 2H, OC$\underline{H}_2CH_aH_bN$), 2.71 (dt, J=11.6, 5.3 Hz, 1H OCH$_2$C$\underline{H}_aH_bN$), 2.62 (dt, J=11.6, 5.5 Hz, 1H, OCH$_2$CH$_a\underline{H}_bN$), 2.5 (sext. J=6.1 Hz, 1H, NC$\underline{H}CH_3$), 2.00–1.95 (m, 2H, C$\underline{H}_2$CH=$CH_2$), 1.47 (bs, 1H, N$\underline{H}$), 1.44–1.35 (m, 3H, C$\underline{H}_2CH_2$CH=$CH_2$ and C$\underline{H}_aH_bCH_2CH_2$CH=$CH_2$), 1.32–1.24 (m, 1H, CH$_a$$\underline{H}_bCH_2CH_2$CH=$CH_2$), 0.99 (d, J=6.8 Hz, 3H, C$\underline{H}_3$), 0.97 (s, 9H, (C$\underline{H}_3$)$_3$CSi), 0.063 (s, 3H, (C$\underline{H}_3$)$_a$Si) 0.061 (s, 3H, (C$\underline{H}_3$)$_b$Si).

Example 6

Preparation of S-(–)-O-tert-butyldimethylsilyl-N-tert-butoxycarbonyl-6-[2-hydroxyethylamino]-1-heptene (6)

To a stirred solution of S-6-[2-tert-butyldimethylsilyloxyethylamino]-1-heptene (5) (1.3 g, 5.0 mmol) in THF (10 mL) was added di-tert-butyldicarbonate (1.2 g, 5.5 mmol). The solution was allowed to stir at rt. for 10 h, then concentrated, and purified by flash chromatography (25 mm×6" column, eluted with 5% v/v EtOAc/hexane) to give 1.77 g of the title compound (6) as a colorless oil (4.9 mmol, 98% yield). $[\alpha]_D^{25}=-1.3°$ (c=4.6, MeOH), $^1H$ NMR (conformeric mixture, 500 MHz $C_6D_6$): δ5.78–5.68 (m, 1H, C$\underline{H}$=$CH_2$), 5.06–4.94 (m, 2H, CH=$CH_2$), 4.36–4.26 (m, 0.5H, NC$\underline{H}CH_3$), 3.81–3.70 (m, 2.5H, NC$\underline{H}CH_3$ and OC$\underline{H}_2CH_2N$), 3.40–3.30 (m, 0.5H, (OCH$_2$C$\underline{H}_aH_bN$), 3.31–3.20 (m, 1H, OCH$_2$CH$_a\underline{H}_bN$), 3.16–3.08 (m, 0.5H, OCH$_2$C$\underline{H}_aH_bN$), 2.02–1.88 (m, 2H, C$\underline{H}_2$CH=$CH_2$), 1.46 (s, 9H, (C$\underline{H}_3$)$_3$CSi), 1.46–1.39 (m, 1H, CH$_a$$\underline{H}\underline{H}_b$(CH$_2$)$_2$CH=$CH_2$), 1.28 (sext. J=7.2 Hz, 2H C$\underline{H}_2CH_2$CH=$CH_2$), 1.22–1.12 (m, 1H, C$\underline{H}_aH_b$(CH$_2$)$_2$CH=$CH_2$), 1.02–0.96 (m, 3H NCHC$\underline{H}_3$), 0.98 (s, 9H, (C$\underline{H}_3$)$_3$CSi), 0.102 (s, 3H, (C$\underline{H}_3$)$_a$Si) 0.099 (s, 3H, (C$\underline{H}_3$)$_b$Si).

Example 7

Preparation of (5Z, 10S)-(–)-N-tert-butoxycarbonyl-10-[2-tert-butyldimethylsilyloxyethylamino]-5-undecenoic acid (7)

[4-carboxybutyl]-triphenylphosphonium ylid was prepared as follows. To a stirred slurry of 4-carboxybutyltriphenylphosphonium bromide (5.89 g, 13.3 mmol) in 20 mL of THF was added 26.5 mL of a 1M solution of potassium hexamethylsilazide in THF. After stirring for 30 min the mixture was centrifuged and the clear, bright orange ylid solution was separated from the solids via syringe.

The title compound was prepared by ozonolysis and a Wittig reaction as follows. 1.6 g (4.4 mmol) of S-(–)-N-tert-butoxycarbonyl-6-[2-tert-butyldimethylsilyloxyethylamono]-1-heptene (6) was taken up in 20 mL of dry tert-butylmethyl ether and cooled to –70° C. A stream of $O_3$ in oxygen was then bubbled through the solution until a faint blue color persisted. After sweeping the solution with dry argon for 10 minutes to remove excess ozone, the above ylid solution was added dropwise at –70° C. The solution was warmed slowly to rt, allowed to stir for 2 h, and then quenched by the addition of 5 mL of $H_2O$. The reaction mixture was washed with a 1:1 mixture of saturated aqueous NaCl and 1N HCl (2×30 mL), and the aqueous layers were back-extracted with $CH_2Cl_2$ (3×30 mL). The combined organic layers were dried ($MgSO_4$), filtered, and concentrated in vacuo to yield 3.9 g of a yellow oil. Purification of the yellow oil by flash chromatography (50 mm×6" column, eluted with 15% v/v EtOAc/hexane containing 1% HOAc) afforded the 1.72 g of the title compound (7) as a viscous, colorless oil (3.7 mmol, 84% yield). $[\alpha]_D^{25}=-3.4°$ (c=2.0, MeOH), $^1H$ NMR (conformeric mixture, 500 MHz, (CD$_3$)$_2$CO): δ10.45 (bs, 1H, RCO$_2\underline{H}$), 5.45–5.34 (m, 2H, RC$\underline{H}$=C$\underline{H}$R'), 4.15–4.04 (m, 0.5H, NC$\underline{H}CH_3$), 3.92–3.83 (m, 0.5H, NC$\underline{H}CH_3$), 3.70 (t, J=6.7 Hz, 2H, OC$\underline{H}_2CH_2N$), 3.22–3.15 (m, 1.5H, OC$\underline{H}_2CH_2N$), 3.14–3.06 (m, 0.5H, OC$\underline{H}_2CH_2N$), 2.30 (t, J=7.4 Hz, 2H, C$\underline{H}_2CO_2H$), 2.14–2.06 (m, 4H, RC$\underline{H}_2$CH=CHC$\underline{H}_2$R'), 1.65 (quin. J=7.4 Hz, 2H, HO$_2$CCH$_2$C$\underline{H}_2$), 1.61–1.50 (m, 1H, CH$_2$C$\underline{H}_aH_b$CHN), 1.49–1.40 (m, 1H, CH$_2$CH$_a\underline{H}_b$CHN), 1.44 (s, 9H, (C$\underline{H}_3$)$_3$COCON), 1.38–1.24 (m, 2H, C$\underline{H}_2$CH$_a$H$_b$CHN), 1.17–1.08 (m, 3H, NCHC$\underline{H}_3$) 0.91 (s, 9H, (C$\underline{H}_3$)$_3$CSi), 0.08 (s, 6H, (C$\underline{H}_3$)$_2$Si).

Example 8

Preparation of (5Z,10S)-(–)-N-tert-butoxycarbonyl-N-[2-tert-butyldimethylsilyloxyethyl]-10-amino-5-undecenoic acid benzyl ester (8)

To a stirred solution of (5Z, 10S)-(–)-N-tert-butoxycarbonyl-10-[2-tert-butyldimethylsilyloxyethylamino]-5-undecenoic acid (8) (100 mg, 0.22 mmol), DMAP (29 mg, 0.24 mmol), and benzyl alcohol (45 μL, 0.44 mmol) in $CH_2Cl_2$ (1.5 mL) was added 24 μL of a 1M $CH_2Cl_2$ solution of DCC. The mixture was stirred at rt for 16 hr, then concentrated, and purified by flash chromatography (15 mm×6" column, eluted with 5% v/v EtOAc/hexane) affording 114 mg of the title compound (8) as a colorless oil (0.21 mmol, 95% yield). $[\alpha]_D^{25}=+0.63°$ C.=2.9, MeOH), $^1H$ NMR (conformeric mixture, 500 MHz $C_6D_6$): δ7.24–7.20 (m, 1H, Ar$\underline{H}$), 7.14–7.05 (m, 4H, Ar$\underline{H}$), 5.41–5.23 (m, 2H, RC$\underline{H}$=C$\underline{H}$R'), 5.02 (s, 2H, ArC$\underline{H}_2CO_2R$), 4.38–4.26 (m, 0.5H, NC$\underline{H}CH_3$), 3.96–3.72 (m, 2.5H, NC$\underline{H}CH_3$ and OC$\underline{H}_2CH_2N$), 3.43–3.12 (m, 2H, OCH$_2$C$\underline{H}_2N$), 2.15 (t, J=7.4 Hz, RO$_2$CC$\underline{H}_2$), 1.96 (quin. J=7.5 Hz, 4H, C$\underline{H}_2$CH=CHC$\underline{H}_2$), 1.63 (quin. J=7.5 Hz, 2H, RO$_2$CCH$_2$C$\underline{H}_2$), 1.52–1.41 (m, 1H, C$\underline{H}_aH_bCH_2$CHN), 1.47 (s, 9H, Boc), 1.33–1.16 (m, 3H, CH$_a\underline{H}_bCH_2$CHN), 1.05–0.98 (m, 3H NCHC$\underline{H}_3$), 0.98 (s, 9H, (C$\underline{H}_3$)$_3$CSi), 0.109 (s, 3H, (C$\underline{H}_3$)$_a$Si) 0.106 (s, 3H, (C$\underline{H}_3$)$_b$Si).

Example 9

Preparation of (5Z,10S)-N-tert-butoxycarbonyl-N-[2-hydroxyethyl]-10-amino-5-undecenoic acid benzyl ester (9)

To a stirred solution of (5Z,10S)-(–)-N-tert-butoxycarbonyl-N-[2-tert-butyldimethylsilyloxyethyl]-10-amino-5-undecenoic acid benzyl ester (8) (100 mg, 0.18 mmol) in 1 mL of THF was added 0.2 mL of a 1M THF solution of tetrabutylammonium fluoride. The mixture was stirred at rt for 16 h, then concentrated, and purified by flash chromatography (11 mm×6" column, eluted with 20% v/v EtOAc/hexane) yielding 76 mg of the title compound (9) as a colorless oil (0.17 mmol, 97% yield). $^1$H NMR (conformeric mixture, 500 MHz, $C_6D_6$): δ7.23–7.20 (m, 1H, ArH), 7.13–6.98 (m, 4H, ArH), 5.39–5.33 (m, 1H, RCH=CHR'), 5.32–5.26 (m, 1H, RCH=CHR'), 5.01 (s, 2H, ArCH$_2$O$_2$CR), 3.85–3.78 (m, 0.5H, NCHCH$_3$), 3.76–3.50 (m, 2.5H, NCHCH$_3$ and OCH$_2$CH$_2$N), 3.21–3.00 (m, 2H, OCH$_2$CH$_2$N), 2.15 (t, J=7.3 Hz, 2H, RO$_2$CCH$_2$), 2.01–1.90 (m, 4H, CH$_2$CH=CHCH$_2$), 1.63 (p, J=7.3 Hz, 2H, RO$_2$CCH$_2$CH$_2$), 1.42 (s, 9H, Boc), 1.31–1.20 (m, 3H, CH$_a$H$_b$CH$_2$CHN), 1.16–1.05 (m, 1H, CH$_a$H$_b$CH$_2$CHN), 0.93–0.82 (m, 3H NCHCH$_3$).

Example 10

Preparation of (5Z,5'Z,10S,10'S)-N-tert-butoxycarbonyl-N-{N'-tert-butoxycarbonyl-N'-[2-tert-butyldimethylsilyloxyethyl]-10'-amino-5'-undecenoyloxyethyl}-10-amino-5-undecenoic acid benzyl ester (10)

To a stirred solution of (5Z,10S)-N-tert-butoxycarbonyl-N-[2-hydroxyethyl]-10-amino-5-undecenoic acid benzyl ester (9)(50 mg, 0.12 mmol), DMAP (17 mg, 0.14 mmol), and DCC (130 μL of 1M CH$_2$CL$_2$ solution) in CH$_2$Cl$_2$ (0.5 mL) was added (5Z,10S)-(−)-N-tert-butoxycarbonyl-10-[2-tert-butyldimethylsilyloxyethylamino]-5-undecenoic acid (7) as its CH$_2$Cl$_2$ solution (53 mg, 0.12 mmol, in 200 μL). The mixture was stirred at rt for 4 hr and then placed directly on a flash column (15 mm×6" column, eluted with 15% v/v EtOAc/Hexane) to give 79 mg of the title compound (10) as a colorless, viscous oil (0.09 mmol, 78% yield). $^1$H NMR (500 MHz $C_6D_6$) δ7.23–7.20 (m, 1H), 7.13–6.98 (m, 4H), 5.51–5.26 (m, 4H), 5.02 (s, 2H), 3.98–3.67 (m, 4H), 3.57–3.01 (m, 6H), 2.30–2.00 (m, 8H), 1.78–1.51 (m, 6H), 1.50–1.48 (bs, 18H), 1.38–1.21 (m, 10H), 1.05–0.96 (m, 15H), 0.08 (s, 6H).

Example 11

Preparation of (5Z,5'Z,10S,10'S)-N-tert-butoxycarbonyl-N-{N'-tert-butoxycarbonyl-N'-[2-hydroxyethyl]-10'-amino-5'-undecenoyloxyethyl}-10-amino-5-undecenoic acid benzyl ester (11)

79 mg (0.09 mmol) of (5Z,5'Z,10S,10'S)-N-tert-butoxycarbonyl-N-{N'-tert-butoxycarbonyl-N'-[2-tert-butyldimethylsilyloxyethyl]-10'-amino-5'-undecenoyloxyethyl}-10-amino-5-undecenoic acid benzyl ester (10) was reacted with tetrabutylammonium fluoride as described for the formation of (5Z,10S)-N-tert-butoxycarbonyl-N-[2-hydroxyethyl]-10-amino-5-undecenoic acid benzyl ester. Purification by flash chromatography (11 mm×6" column eluted with 35% v/v EtOAc/hexane) yielded 63 mg of the title compound (11) as a colorless oil (0.083 mmol, 92% yield).

Example 12

Preparation of (5Z,5'Z,5"Z,10S,10'S,10"S)-N-tert-butoxycarbonyl-N-{N'-tert-butoxycarbonyl-N'-(2"-tert-butoxycarbonyl-N"-[2-tert-butyldimethylsilyloxyethyl]-10"-amino-5"-undecenoyloxyethyl)-10'-amino-5'-undecenoyloxyethyl}-10-amino-5-undecenoic acid benzyl ester (12)

60 mg (79 μmol) of (5Z,5'Z,10S,10'S)-N-tert-butoxycarbonyl-N-{N'-tert-butoxycarbonyl-N'-[2-hydroxyethyl]-10'-amino-5'-undecenoyloxyethyl}-10-amino-5-undecenoic acid benzyl ester (11) was combined with DMAP (12 mg, 95 μmol), DCC (100 μL of 1M CH$_2$Cl$_2$ solution.), and (5Z,10S)-(−)-N-tert-butoxycarbonyl-10-[2-tert-butyldimethylsilyloxyethylamino]-5-undecenoic acid (7) as its CH$_2$Cl$_2$ solution (39 mg, 85 μmol). After stirring for 5 h at rt., the entire reaction mixture was then placed directly on a flash column (15 mm×6") and eluted with 20% v/v EtOAc/hexane to give 69 mg of the title compound (12) as a colorless oil (57 μmol 72% yield). $^1$H NMR (500 MHz $C_6D_6$) δ7.24–7.20 (m, 1H), 7.15–6.98 (m, 4H), 5.54–5.22 (m, 6H), 5.02 (s, 2H), 3.98–3.65 (m, 6H), 3.62–3.01 (m, 9H), 2.38–1.95 (m, 12H), 1.82–1.51 (m, 9H), 1.50–1.48 (bs, 27H), 1.46–1.21 (m, 15H), 1.05–0.96 (m, 18H), 0.08 (s, 6H).

Example 13

Preparation of (5Z,5'Z,5"Z, 10S,10'S,10"S)-N-tert-butoxycarbonyl-N-{N'-tert-butoxycarbonyl-N'-(2"-tert-butoxycarbonyl-N"-[2-hydroxyethyl]-10"-amino-5"-undecenoyloxyethyl)-10'-amino-5'-undecenoyloxyethyl}-10-amino-5-undecenoic acid benzyl ester (13)

To a stirred THF (0.25 mL) solution of (5Z,5'Z,5"Z,10S, 10'S,10"S)-N-tert-butoxycarbonyl-N-{N'-tert-butoxycarbonyl-N'-(2"-tert-butoxycarbonyl-N"-[2-tert-butyldimethylsilyloxyethyl]-10"-amino-5"-undecenoyloxyethyl)-10'-amino-5'-undecenoyloxyethyl}-10-amino-5-undecenoic acid benzyl ester (12) (50 mg, 41 μmol) was added TBAF (45 μL of 1M solution). The reaction mixture was stirred for 16 h and then concentrated to give the titlecompound (13), which was used in the next reaction without further purification.

Example 14

Preparation of (10S,10'S,10"S)-N-tert-butoxycarbonyl-N-{N'-tert-butoxycarbonyl-N'-(2"-tert-butoxycarbonyl-N"-[2-hydroxyethyl]-10"-amino-5"-undecanoyloxyethyl)-10'-amino-5'-undecanoyloxyethyl}-10-amino-5-undacenoic acid (14)

Crude (5Z,5'Z,5"Z,10S,10'S,10"S)-N-tert-butoxycarbonyl-N-{N'-tert-butoxycarbonyl-N'-(2"-tert-butoxycarbonyl-N"-[2-hydroxyethyl]-10"-amino-5"-undecenoyloxyethyl)-10'-amino-5'-undecenoyloxyethyl}-10-amino-5-undecenoic acid benzyl ester (13) from the above reaction was taken up in MeOH (0.5 mL). 10 mg of 5% Pd/C was added, and the slurry was stirred under 10 psi H$_2$ for 20 h at rt. The reaction mixture was then filtered and concentrated. The residue was taken up in 5 mL of ether. The ether solution was then washed with saturated aqueous NaCl (2×5 mL), dried (MgSO$_4$), filtered, and concentrated to give 38 mg of the title compound (14) as a clear, colorless oil. This oil was used without further purification in the next reaction.

Example 15

Preparation of the N,N',N"-tris-tert-butoxycarbonyl Derivative of PAML 681 (15)

A mixture of (10S,10'S,10"S)-N-tert-butoxycarbonyl-N-{N'-tert-butoxycarbonyl-N'-(2"-tert-butoxycarbonyl-N"-[2-hydroxyethyl]-10"-amino-5"-undecanoyloxyethyl)-10'-amino-5'-undecanoyloxyethyl}-10-amino-5-undacenoic acid (14) (38 mg, 38 μmol) and Et$_3$N (42 μL, 302 μmol) was taken up in CH$_3$CN (1 mL) and added to a refluxing solution of Mukaiyama salt (2-chloro-N-methylpyridinium iodide) (39 mg, 151 μmol) in 50 mL of CH$_3$CN via syringe pump over the course of two hours. After the addition was complete, the solution was refluxed for an additional 30 min, then cooled to rt, and concentrated at reduced pressure to give a solid orange residue. This residue was taken up in H$_2$O (5 mL) and extracted with ether (5×3 mL). The combined organic extracts were dried (MgSO$_4$), filtered, and concentrated in vacuo to afford 43 mg of a yellow oil. The yellow oil was purified by flash chromatography (11 mm×4" column, eluted with 10% EtOAc/hexane) to give 14 mg of the title compound (15) as a colorless oil (14 mol 37% yield).

Example 16

Preparation of PAML 681 (16)

1.0 mg (1.0 μmol) of the N,N',N"-tris-tert-butoxycarbonyl derivative of PAML-681 (15) was taken up in neat CF$_3$CO$_2$H (10 μL) and allowed to sit for 15 minutes. The excess acid was then evaporated at reduced pressure, and 1 mL of ether and 100 μL of 20% aqueous K$_2$CO$_3$ was added. After vigorous mixing, the organic layer was separated, and the aqueous layer was extracted with ether (2×1 mL). The combined organic fractions were filtered through a plug of anhydrous K$_2$CO$_3$ and concentrated to give 570 μg (0.84 μmol, 84% yield) of pure PAML 681 (16). $^1$H NMR (500 MHz, C$_6$D$_6$): δ (ppm) 0.97 (d, J=6.4 Hz, 9H,), 1.19–1.41 (m, 36H), 1.63 (quin., J=7.1 Hz, 6H), 2.20 (t, J=7.4 Hz, 6H), 2.49–2.56 (m, 3H,), 2.63 (ddd, J=12.7, 6.8, 4.4 Hz, 3H), 2.72 (ddd, J=12.7, 6.3, 4.3 Hz, 3H), 4.14 (ddd, J=11.1, 6.8, 4.4 Hz, 3H), 4.20 (ddd, 11.1, 6.8, 4.3 Hz, 3H).

Example 17

Insect Repellency and Irritancy Testing

Feeding tests, conducted using PAML (16) and other macrocycles of the present invention, with beetles (Carabidae) and irritancy tests with cockroaches of the species Periplaneta americana (American cockroach) showed that PAML 681 (16) is a strong insect repellent and deterrent.

Example 18

Comparative Study of the Secretion of Coccinellid Pupal Hairs

Figure 1C:
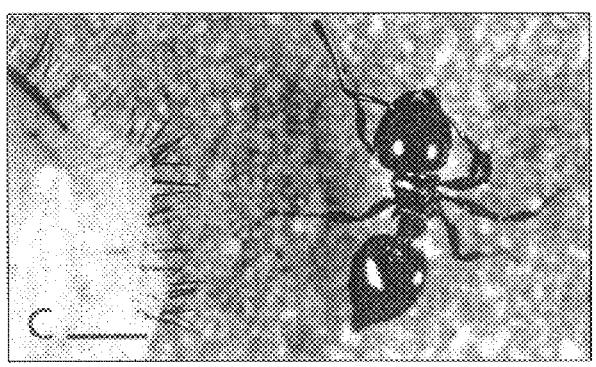
Figure 2:
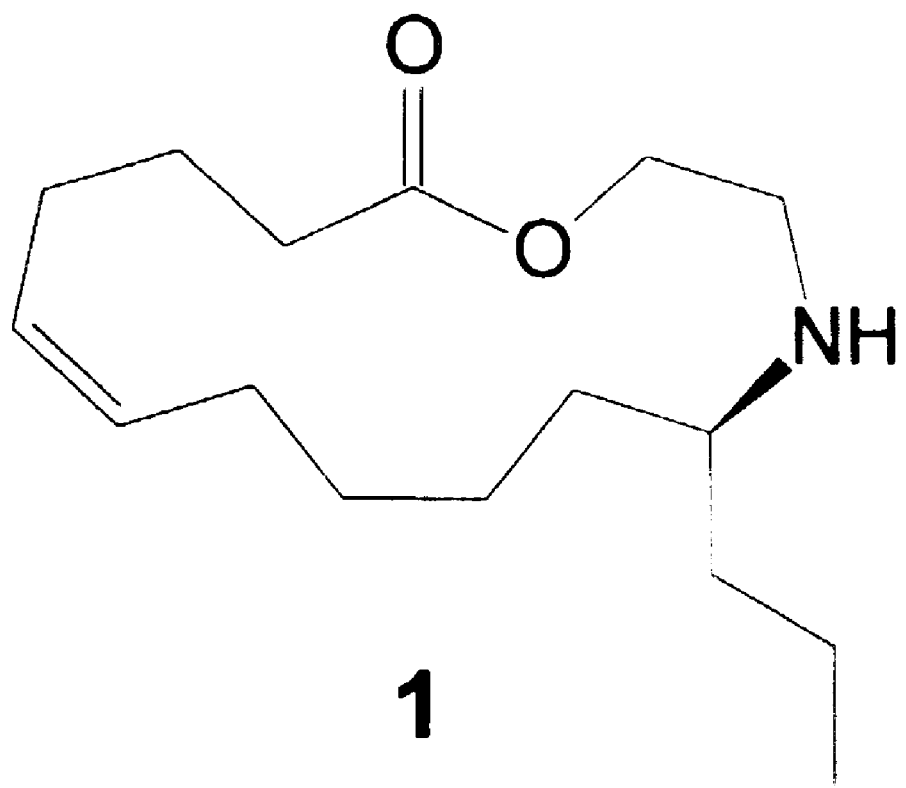
FIG. 2 is the chemical formula for epilachnene, the chief azamacrolide in the pupal defensive secretion of *E. varivestis*.
Figure 3:
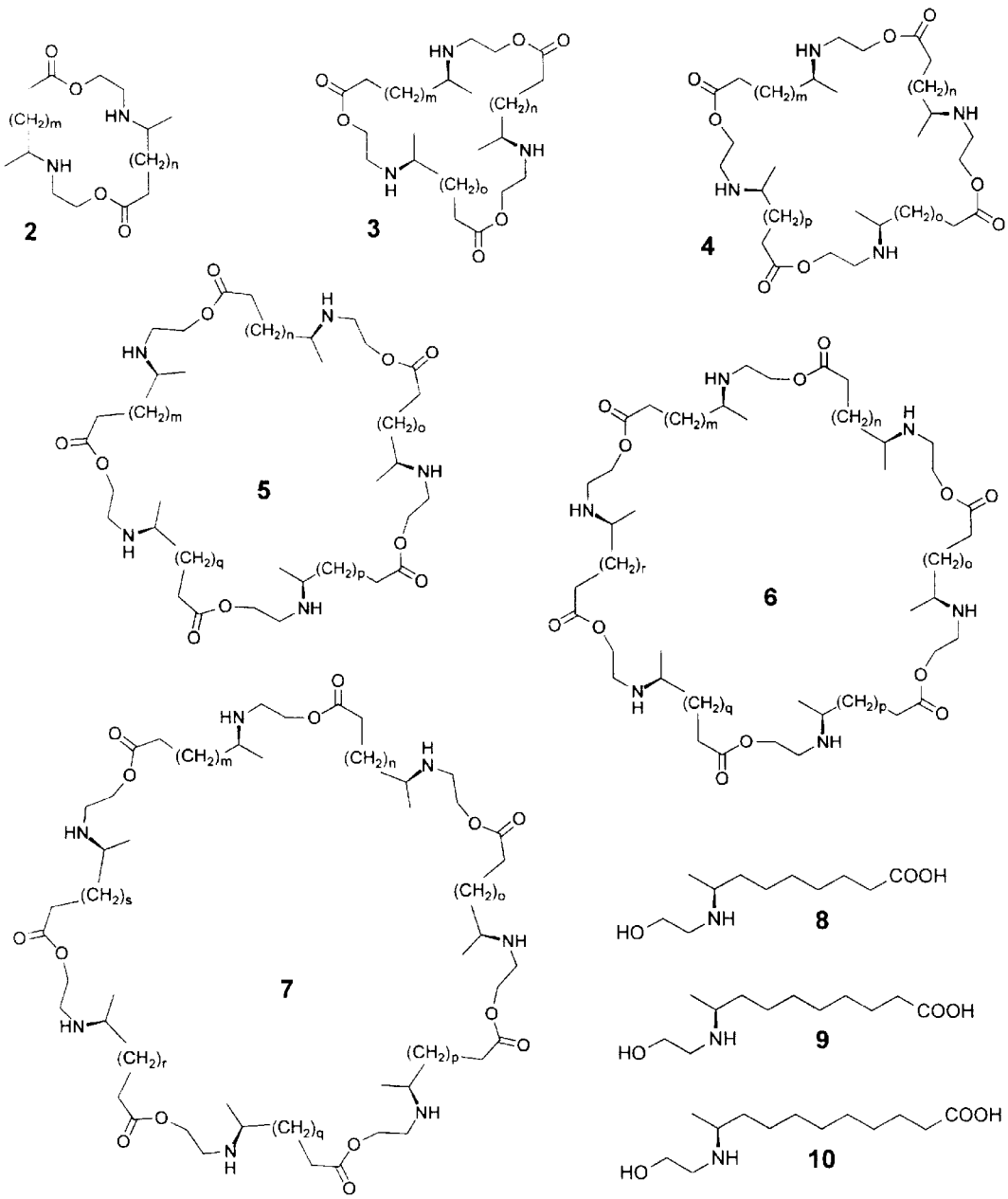
FIG. 3 is a library of macrocyclic polyazamacrolides ("PAMLs") of the present invention corresponding to the set of bis- to heptalactones (structures 2–7) derivable from three homologous (ω-1)-(2-hydroxyethylamino)alkanoic acids (structures 8–10).
Figure 4:
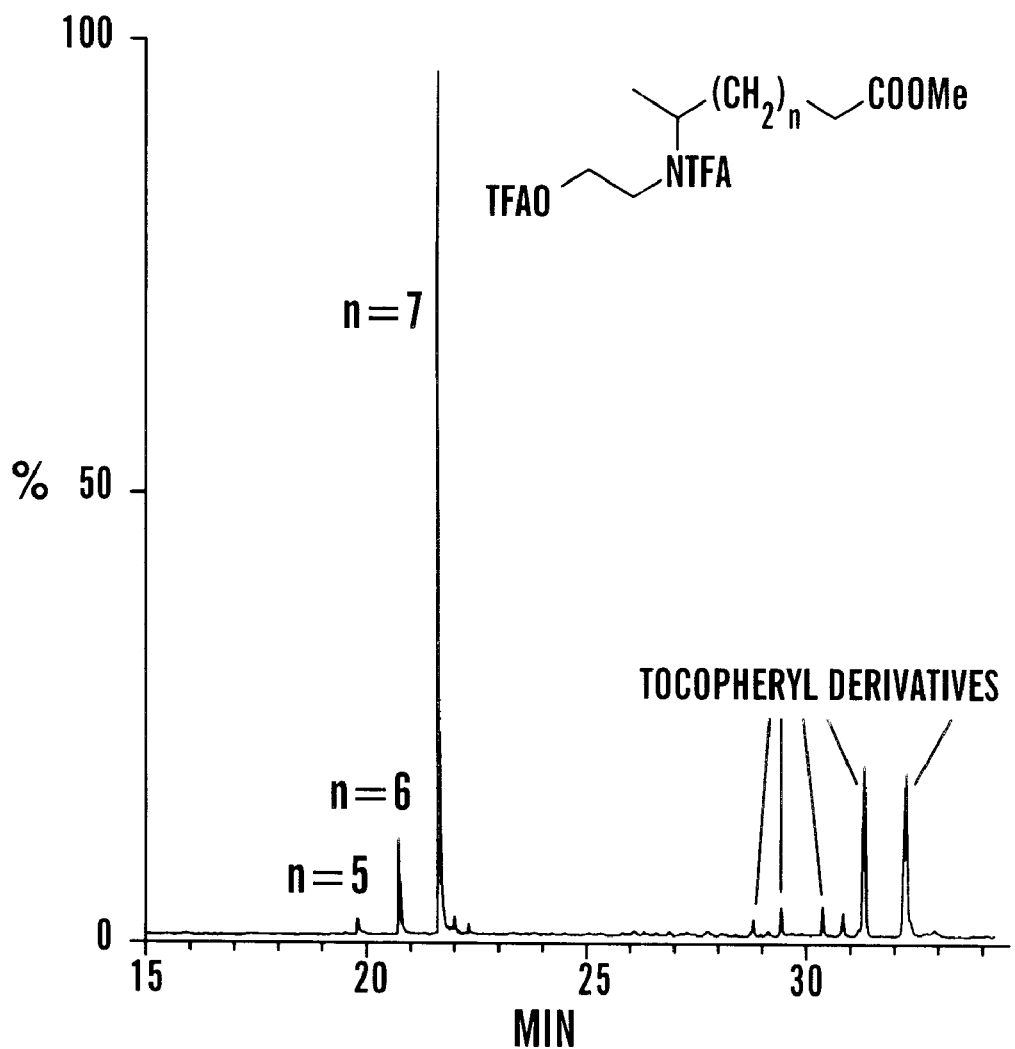
FIG. 4 is a GC/MS chromatogram of hydrolyzed pupal secretion after methylation and trifluoroacetylation showing the relative abundances of the derivatives of the (ω-1)-(2-hydroxyethylamino)alkanoic acids (structures 8–10 of FIG. 3) are 1.5:8.5:90, respectively.
Figure 5A:
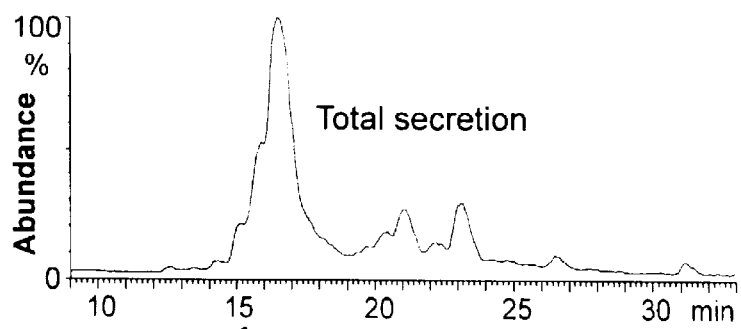
FIG. 5 is a HPLC-MS analysis of *E. borealis* pupal secretion, taken from 4-day-old pupae; (A): total ion current ("TIC") chromatogram. (B), (C), and (D): ion chromatograms for the pseudo molecular ions $(M+H)^+$ of each five homologous trimers, tetramers, and pentamers, respectively, showing several series of isomers. For each of the displayed ion chromatograms, the largest peak is normalized to 100%. X: peaks representing components that were isolated by preparative HPLC.
Figure 5B:
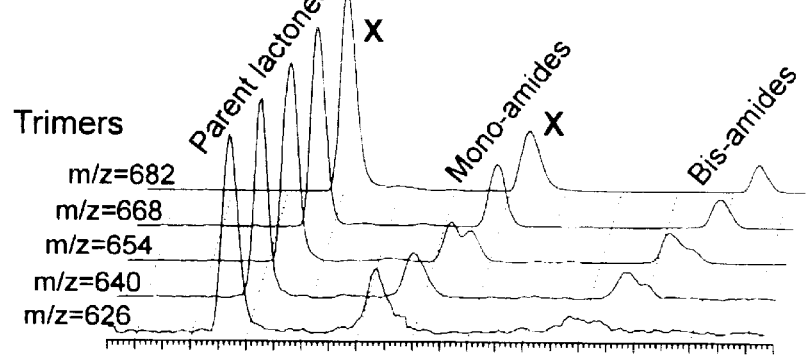
Figure 5C:
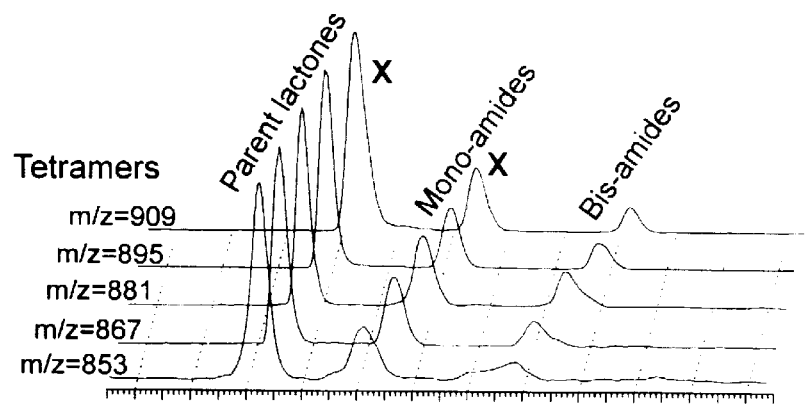
Figure 5D:
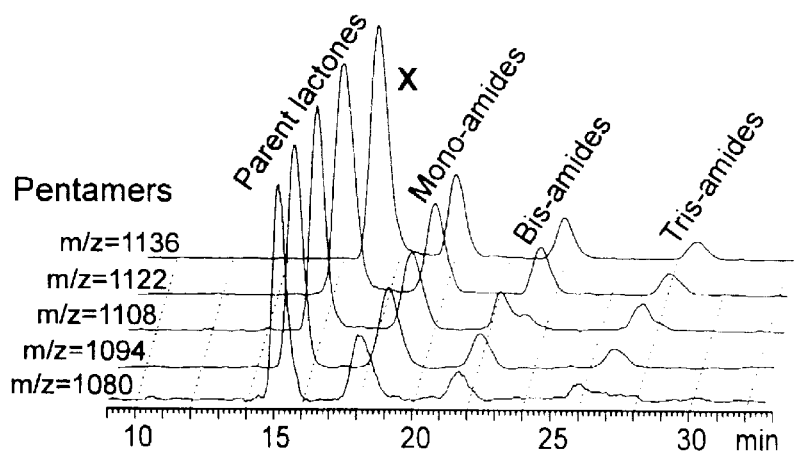

A comparative study of the secretion of coccinellid pupal hairs was conducted to determine if natural variants of azamacrolides existed, as disclosed by Schroeder, Frank, et al., "Combinatorial Chemistry in Insects: A Library of Defensive Macrocyclic Lactones Produced by a Ladybird Beetle", Science, 281: 428–431 (1998) ("Schroeder"), incorporated herein by reference. It was discovered that the glandular material of the squash beetle (*Epilachna borealis*) is largely a mixture of saturated macrocyclic molecules biosynthetically related to the azamacrolides, but with much larger ring sizes, i.e. 24 to 98 members, as shown in FIG. 3, corresponding to the set of bis- to heptalactones (structures 2–7 of FIG. 3) derived from three homologous (ω-1)-(2-hydroxyethylamino)alkanoic acids (structures 8–10 of FIG. 3), which represent a library of macrocycles comprising cyclic polyamino lactones, or polyazamacrolides ("PAML"), generated by an apparently non-selective oligomerization of these three acids. Gas chromatographic analysis of *E. borealis* secretion samples revealed only vitamin E acetate and other tocopherol derivatives. However, in tests with ants these compounds proved to be essentially inactive, while the secretion itself was potently deterrent, as demonstrated by FIG. 1C. Three to five day old *E. borealis* pupae were washed with 0.2 ml of dichloromethane. The combined washings of 30–60 pupae were evaporated in vacuo. Subsequently, the oily, colorless and odorless residue was dissolved in 0.6 ml of NMR solvent and directly submitted to NMR-analysis. Unexpectedly, one- and two-dimensional $^1$H-NMR experiments revealed that the tocopheryl acetates account for only a relatively small percentage of the beetles' total secretion (~20%), while the major components represented a group of previously undetected compounds. By analysis of ($^1$H,$^1$H)-E.COSY, (13C,1H)-HMQC, and HMBC spectra of the mixture, these components were shown to be esters and amides derived from the carboxyl-and the 2-hydroxyethylamino-moieties of several (ω-1)-(2-hydroxyethylamino)alkanoic acids. The chain lengths of these acids were determined by GC-MS. The crude secretion was prepared for analysis by alkaline hydrolysis of the crude secretion, followed by methylation with diazomethane and trifluoroacetylation with trifluoroacetic acid anhydride to produce a mixture. The mixture was then injected into a Hewlett-Packard ("HP") 5890 II gas chromatograph linked to a HP 5970 mass selective detector under the following specifications: column: 30 m fused silica DB5-MS, film 0.25 μm, i.d. 0.25 mm; conditions: 3 min at 80° C., then increased at a rate of 10° C./min. to 290° C. As shown in FIG. 4, analysis of the mixture revealed N,O-bis-trifluoroacetylated methyl esters of three homologous (ω-1)-(2-hydroxyethylamino)alkanoic acids having chemical structures 8–10 of FIG. 3. The major component (~90%) of the alkaline hydrolysate, 10-(2-hydroxyethylamino)undecanoic acid, structure 10 of FIG. 3, was isolated by column chromatography and characterized by its $^1$H- and $^{13}$C-NMR spectra. $^1$H-NMR (500 MHz, CD$_3$OD) δ (ppm) 1.31 (d, J=6.5 Hz, 3 H), 1.33–1.49 (m, 8 H), 1.50–1.65 (m, 3 H, 11-H), 1.74–1.81 (m, 1 H), 2.28 (t, J=7.2 Hz, 2 H, 2-H), 3.08–3.16 (m, 2 H, CH$_2$—N), 3.22–3.30 (m, 1 H, 10-H), 3.79 (t, J=7.0 Hz, 2 H, CH$_2$—O); $^{13}$C-NMR (126 MHz, CD$_3$OD) δ (ppm) 16.0, 25.9, 29.9, 30.0, 30.0, 30.1, 30.2, 33.7, 34.7, 47.4, 55.4, 57.8, 177.7.

HPLC-analyses were conducted using a mass-spectrometric detector, which revealed the secretion to contain a highly diverse mixture of polyazamacrolides, as shown in FIG. 5. A HP 1090 II pump was linked to a Micromass Quattro I mass spectrometer operated in positive ion electrospray mode under the following specifications: HPLC-column: 250×46 mm Inertsil 5μ ODS-3 (Metachem); flow 0.7 ml/min.; solvent gradient system: from a mixture of 95% water, 4.5% acetonitrile, 0.4% tetrahydrofuran, and 0.1% formic acid to 60% water, 22% acteonitrile, 17.9% tetrahydrofuran, and 0.1% formic acid over a period of 32 minutes. The major components are a series of homologous trimers, tetramers, and pentamers of the three (ω-1)-(2-hydroxyethylamino)alkanoic acids, along with smaller quantities of dimers, hexamers, and heptamers. Using repeated preparative HPLC fractionation, the most abundant trimeric, tetrameric, and pentameric compounds were isolated utilizing the HPLC-system and column described immediately above under the following specifications: flow 1.1 ml/min.; solvent gradient system: from a mixture of 95% water, 4% acetonitrile, 0.94% tetrahydrofuran, and 0.06% formic acid to 84% water, 9.5% acteonitrile, 6.44% tetrahydrofuran, and 0.06% formic acid over a period of 45 minutes. These polyazamacrolides were isolated in 70–90% purity. The monoamide trimer of structure 15 shown in FIG. 8 and the corresponding monoamide tetramer were isolated by again using the HPLC-conditions of the HP 1090 II pump and Micromass Quattro I mass spectrometer described above. One- and two-dimensional $^1$H-NMR spectroscopic analyses showed these components to be symmetric macrocyclic lactones, chemical structures 3, 4, and 5 of FIG. 3, derived from three, four, or five units of 10-(2-hydroxyethylamino)undecanoic acid (see chemical structure 10 of FIG. 3).

Figure 6:
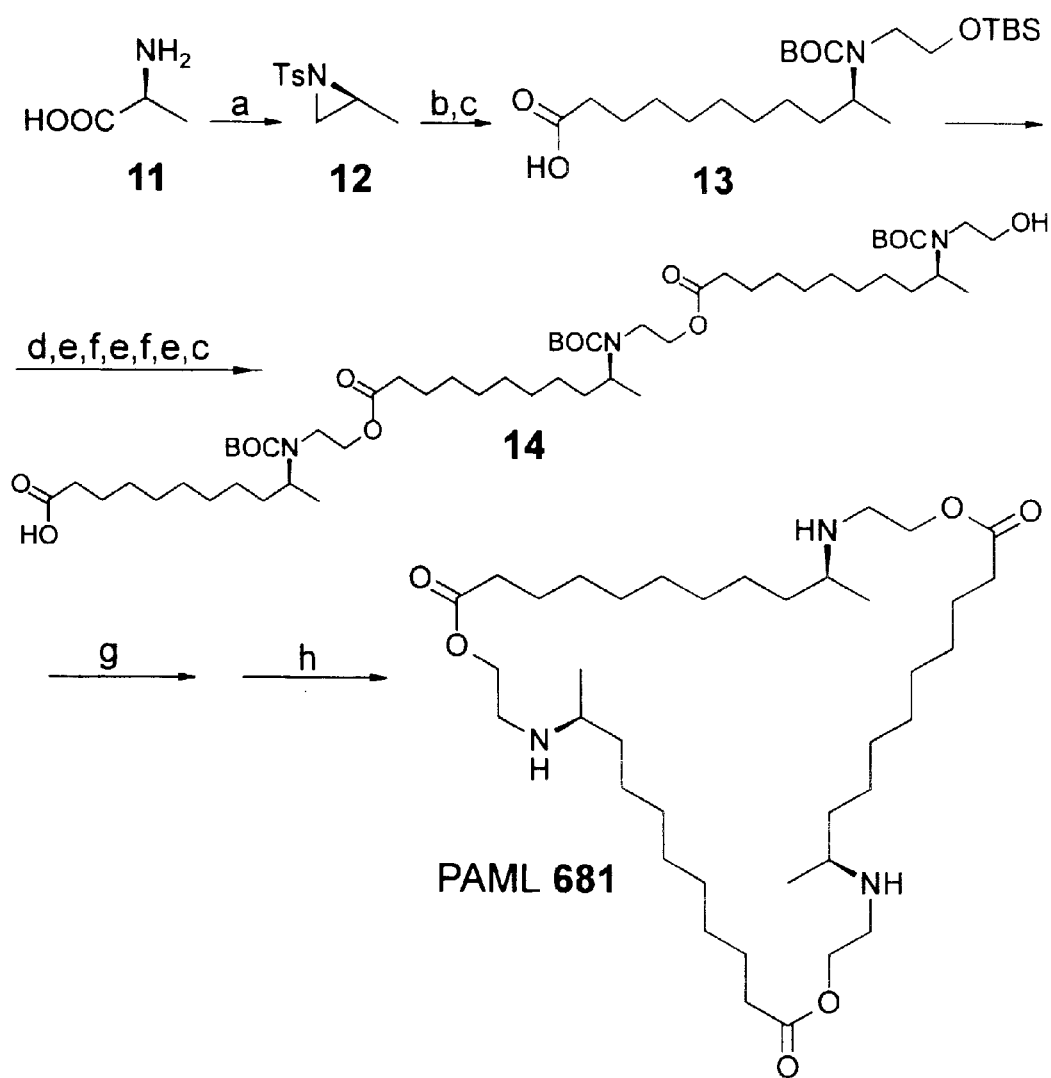
FIG. 6 shows the synthesis of the most abundant polyazamacrolide, PAML 681. a: 1. $LiBH_4$, TMSCl, TFA; 2. TsCl, pyridine, $CH_2Cl_2$; 3. $K_2CO_3$, acetone. b: 1. Bis-(3-butenyl)magnesium, CuI, $Et_2O$; 2. NaH, Br$(CH_2)_2$OTBDMS; 3. Sodium naphthalide, DME; 4. $Boc_2O$, THF; 5. $O_3$, $CH_2Cl_2$; 6. KHMDS, $PPh_3(CH_2)_4CO_2H$,THF. c: $H_2$, Pd/C, MeOH. d. BnOH, DCC, DMAP, $CH_2Cl_2$. e: $Bu_4NF$, THF. f: compound 13 of FIG. 6, DCC, DMAP, $CH_2Cl_2$. g. Mukaiyama salt, $Et_3N$, $CH_3CN$, high dilution. h: $CF_3CO_2H$, neat.

Referring to FIG. 6, the total synthesis of the most abundant trimer, PAML 681, is detailed. The stepwise reaction conditions, which are discussed in detail in Examples 2–16, are as follows:

a: 1. LiBH$_4$, TMSCl, TFA (see Giannis, A., et al., "LiBH4 (NaBH4)/Me3SiCl, An Unusually Strong and Versetile Reducing Agent", *Angew. Chem. Int. Ed. Engl.*, 28: 218 (1989), incorporated herein by reference); 2. TsCl, pyridine, CH$_2$Cl$_2$; 3. K$_2$CO$_3$, acetone. b: 1. Bis-(3-butenyl)magnesium, CuI, Et$_2$O; 2. NaH, Br(CH$_2$)$_2$OTBDMS; 3. Sodium naphthalide, DME; 4. Boc$_2$O, THF; 5. O$_3$, CH$_2$Cl$_2$; 6. KHMDS, PPh$_3$(CH$_2$)$_4$CO$_2$H, THF. c: H$_2$, Pd/C, MeOH. d. BnOH, DCC, DMAP, CH$_2$Cl$_2$. e: Bu$_4$NF, THF. f: compound 13 of FIG. 6, DCC, DMAP, CH$_2$Cl$_2$. g. Mukaiyama salt, Et$_3$N, CH$_3$CN, high dilution (see Mukaiyama, T., et al., "An Efficient Method for the Synthesis of Nacrocyclic Lactone", *Chem. Lett.*, 4: 441–4 (1977). h: CF$_3$CO$_2$H, substantially pure.

As shown, a linear 10-(2-hydroxyethylamino)undecanoic acid trimer (chemical structure 14 of FIG. 6) was prepared from L-alanine (chemical structure 11 of FIG. 6). Thereafter, the trimer was cyclized. The final product was indistinguishable from the purified natural material in its NMR- and HPLC-MS properties.

Figures 7A, 7B:
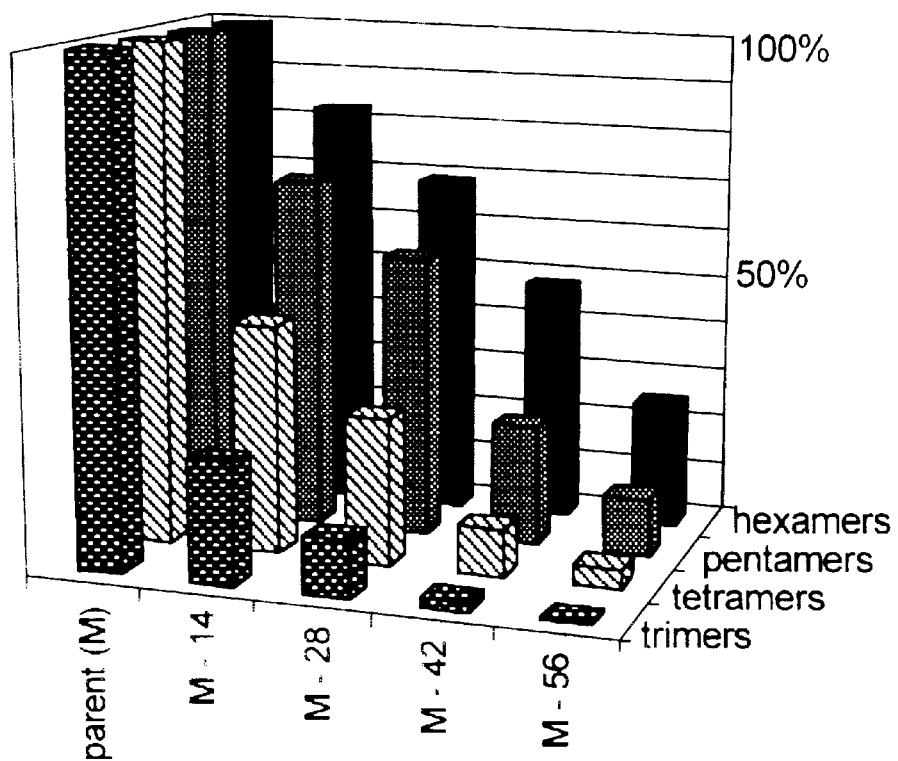
FIG. 7A represents the relative amounts of each of the oligomer series of PAML in *E. borealis* pupal secretion; M: nominal molecular mass; Σ: estimated relative amounts of each of the oligomers, based on the relative abundance of corresponding molecular ions obtained by LC-MS.
FIG. 7B shows relative abundances (%) of the series of homologues, the column representing the parent component (the oligomer made up entirely from the acid of structure 10 of FIG. 3) is normalized to 100%.

FIG. 7A shows the nominal molecular masses of all the dimers, trimers, tetramers, pentamers, hexamers, and heptamers (structures 2–7, respectively, of FIG. 3). Evidence from this research indicates that the three basic building blocks, structures 8–10 of FIG. 3, are incorporated into the polyazamacrolides in random fashion, producing a series of homologues of each oligomer, as shown by FIG. 7B.

Figure 8:
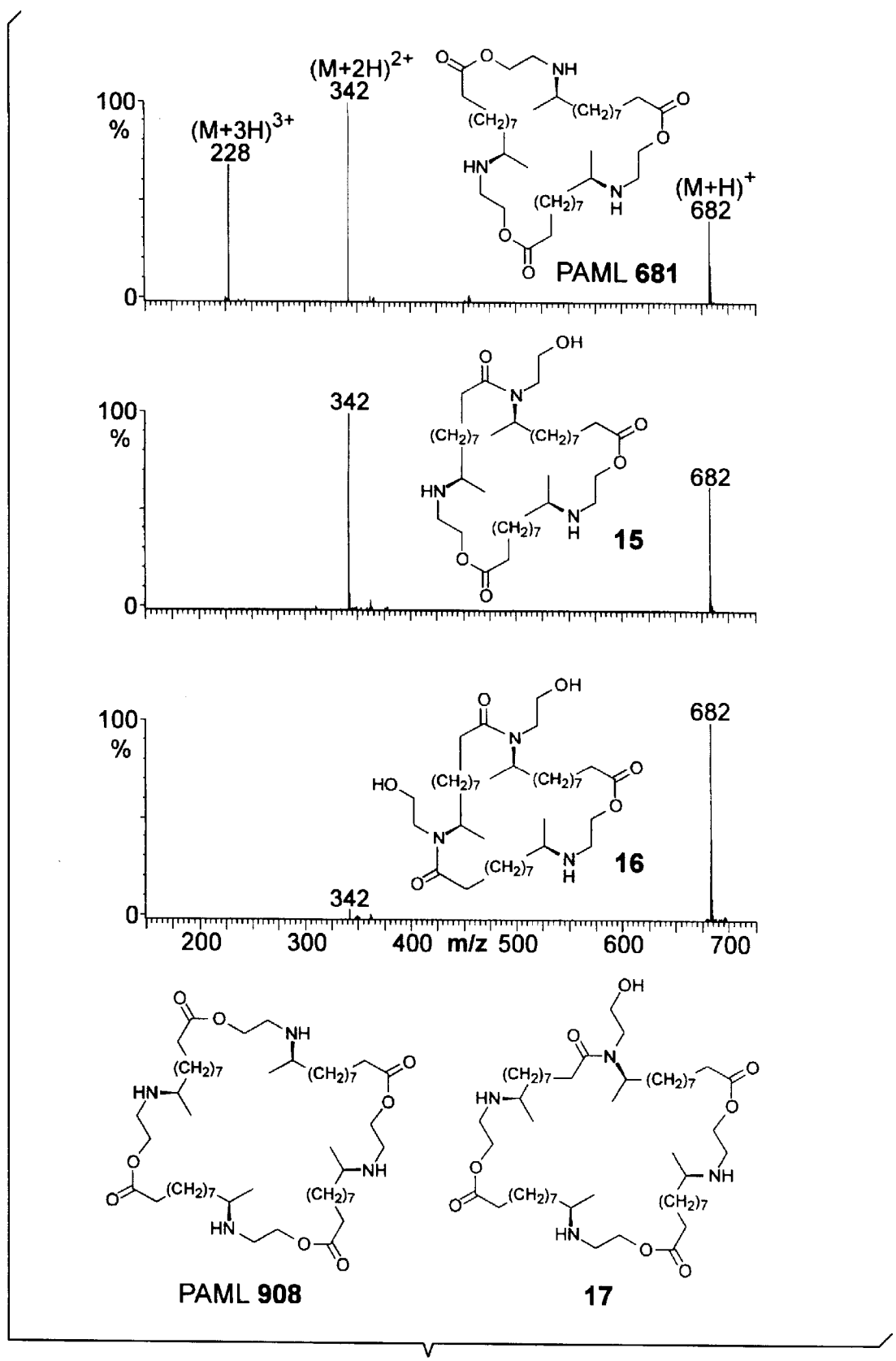
FIG. 8 shows the positive ion electrospray mass spectra of three isomers of the most abundant trimer (nominal molecular mass M=681). The spectrum of the tris-lactone PAML 681 shows ions $(M+3H)^{3+}=228$, $(M+2H)^{2+}=341$, and $(M+H)^{+}=682$, the mono-amide 15 only $(M+2H)^{2+}=341$ and $(M+H)^{+}=682$, and the bis-amide 16 predominantly $(M+H)^{+}=682$.

Again referring to FIG. 5 and additionally to FIG. 8, further analysis of the secretion by HPLC-MS indicated the presence of several isomers of each of the parent PAML's, comprising structures 2–7 of FIG. 3. Unexpectedly, the members of any given group of isomers showed strikingly different mass spectra. The most abundant trimers, tetramers, and pentamers (structures 3–5 of FIG. 3, respectively) produced multiple charged cations with up to three, four, or five charges, respectively, corresponding to the number of basic nitrogen atoms in each compound. As indicated in FIG. 8, the later-eluting isomers of each of these parents did not achieve this degree of protonation. The second series of trimers, for example, produced mostly singly and doubly charged pseudomolecular ions, (M+H)$^+$ and (M+2H)$^{2+}$, while the third series of trimers showed predominantly singly charged ions (M+H)$^+$.

The most abundant components of the later-eluting, second series of trimers and tetramers (see FIG. 5) were isolated by repeated preparative HPLC fractionation as described above. NMR-spectroscopic analyses showed the isolated trimer comprising three units of the hydroxy amino acid having structure 10 of FIG. 3, which are connected by two ester linkages plus one amide linkage (structure 15 of FIG. 8). $^1$H-NMR-data of the monoamide trimer, structure 15 of FIG. 8, (500 MHz, C$_6$D$_6$) δ (ppm) 0.71 (d, J=6.4 Hz, 3 H, 11-H of N-acylated unit), 0.95 (m, 1 H, 9-H$_a$ of N-acylated unit), 0.97 (d, J=6.4 Hz, 6 H, 11-H of O-acylated unit), 1.10 (m, 1 H, 9-H$_b$ of N-acylated unit), 1.18–1.52 (m, 34 H, 4, 5, 6, 7, and 8-H of all three units and 9-H of O-acylated units), 1.57–1.83 (m, 6 H, 3-H of all three units), 2.09–2.16 (m, 1 H, 2-H$_a$ of N-acyl unit), 2.16–2.24 (m, 1 H, 2-H$_b$ of N-acyl unit), 2.19–2.24 (m, 4 H, 2-H of O-acyl units), 2.48–2.55 (m, 2 H, 10-H of O-acylated units), 2.58–2.64 (ddd-like m, 2 H, N—C$\underline{H}_a$H$_b$ of O-acylated units), 2.68–2.75 (m, 2 H, N—CH$_a$$\underline{H}_b$ of O-acylated units), 3.15 (dt, J$_{N—C\underline{H}aHb,N—CHa\underline{H}b}$=14.1 Hz, J$_{N—C\underline{H}aHb,O—C\underline{H}aHb}$=5.5 Hz, 1 H, N—C$\underline{H}$aHb of N-acylated unit), 3.32 (dt, J$_{N—C\underline{H}aHb,N—CHa\underline{H}b}$=14.1 Hz, J$_{N—CHa\underline{H}b,O—C\underline{H}aHb}$=5.5 Hz, 1 H, N—CH$_a$$\underline{H}_b$ of N-acylated unit), 3.39–3.47 (m, 1 H, 10-H of N-acylated unit), 3.72–3.76 (m, 2 H, C$\underline{H}_2$—OH), 4.11–4.17 (m, 2H, O—C$\underline{H}_a$H$_b$ of O-acylated units), 4.18–4.24 (m, 2 H, O—CH$_a$$\underline{H}_b$ of O-acylated units). Since the monoamide of structure 15 has one basic center less than the all-lactonic isomer PAML 681, it shows less highly protonated pseudomolecular ions in its electrospray mass spectra, as indicated in FIG. 8. NMR and mass spectroscopic studies on the isolated tetramer yielded analogous results consistent with structure 17.

Again referring to FIG. 5, the mass spectroscopic properties of the later-eluting isomers of the polyazamacrolides (structures 2–7 of FIG. 3) result in their characterization as compounds with one or more amide linkages and a correspondingly reduced number of ester linkages. By using isolated samples of the most abundant entirely lactonic trimer (PAML 681), tetramer (PAML 908), and pentamer (PAML 1135, which comprises structure 5 of FIG. 3, wherein m, n, o, p, and q=7), it is shown that the corresponding isomeric compounds with one or more amide linkages form spontaneously. To estimate the rate of isomerization, substantially pure samples of PAML 681, PAML 908, and PAML 1135 were stored at 25° C. for 2 days. Subsequent analyses by HPLC-MS revealed 7%, 10%, and 12% of monoamide (relative percentage of the total ion current) for the trimer, tetramer and pentamer, respectively. Therefore, it is shown that intramolecular O-to-N acyl transfer can proceed through a favorable five-membered ring intermediate, especially since the amides are generally more stable than the esters.

$^1$H-NMR-data of PAML 681 (500 MHz, C$_6$D$_6$) δ (ppm) 0.97 (d, J=6.4 Hz, 9 H, 11-H), 1.19–1.41 (m, 36 H, 4, 5, 6, 7, 8, and 9-H),1.63 (quin., J=7.1 Hz, 6 H, 3-H), 2.20 (t, J=7.4 Hz, 6 H, 2-H), 2.49–2.56 (m, 3 H, 10-H), 2.63 (ddd, J$_{N—C\underline{H}aHb}$=12.7 Hz, J$_{N—C\underline{H}aHb,O—C\underline{H}aHb}$=6.8 Hz, J$_{N—C\underline{H}aHb,O—CHa\underline{H}b}$=4.4 Hz, 3 H, N—C$\underline{H}_a$H$_b$), 2.72 (ddd, J$_{N—CHa\underline{H}b,O—C\underline{H}aHb}$=4.3 Hz, J$_{N—CHa\underline{H}b,O—CHa\underline{H}b}$=6.3 Hz, 3 H, N—CH$_a$$\underline{H}_b$), 4.14 (ddd, J$_{O—C\underline{H}aHb}$=11.1 Hz, 3 H, O—C$\underline{H}_a$H$_b$), 4.2 (ddd, 3 H, O—CH$_a$$\underline{H}_b$).

$^1$H-NMR-data of PAML 908 (500 MHz, C$_6$D$_6$) δ (ppm) 0.98 (d, J=6.2 Hz, 12 H, 11-H), 1.19–1.43 (m, 48 H, 4, 5, 6, 7, 8, and 9-H), 1.60–1.67 (m, 8 H, 3-H), 2.22 (t, J=7.4 Hz, 8 H, 2-H), 2.50–2.57 (m, 4 H, 10-H), 2.65 (ddd, J$_{N—C\underline{H}aHb}$=12.6 Hz, J$_{N—C\underline{H}aHb,O—CHa\underline{H}b}$=6.7 Hz, J$_{N—C\underline{H}aHb,O—C\underline{H}aHb}$=4.5 Hz, 3 H, N—C$\underline{H}$aHb), 2.74 (ddd, J$_{N—CHa\underline{H}b,O—C\underline{H}aHb}$=4.6 Hz, J$_{N—CHa\underline{H}b,O—CHa\underline{H}b}$=6.3 Hz, 4 H, N—CH$_a$$\underline{H}_b$), 4.14–4.19 (m, 4 H, O—C$\underline{H}_a$H$_b$), 4.19–4.23 (m, 3 H, O—CH$_a$$\underline{H}_b$). The $^1$H-NMR chemical shift values of PAML 1135 closely resemble those given for PAML 908.

Thus, the glandular material of *E. borealis* is largely a mixture of saturated macrocyclic molecules biosynthetically related to the azamacrolides, but with larger ring sizes of 24 to 98 members, corresponding to the set of bis- to heptalactones, structures 2–7 of FIG. 3, derivable from three homologous (ω-1)-(2-hydroxyethylamino)alkanoic acids, structures 9–10 of FIG. 3. This novel family of cyclic polyamino lactones, or polyazamacrolides, represents a library of macrocycles, generated by non-selective oligomerization of these three acids.

Example 19

Insect Repellency and Irritancy Testing of Synthetic Macrocycles

Synthetic samples of macrocycles PAML 681, PAML 908, and PAML 1362 (structure 6 of FIG. 3, wherein m, n, o, p, q, and r=7) as well as mixtures of synthetic PAML 681 and Vitamin E acetate were used in bioassays with various predacious insects, for example, ladybird beetles (*Harmonia axyridis*) and ants of the genus Crematogaster. In these bioassays, all of the aforementioned formulations were biologically highly active as insect deterrents. A mixture of 80 weight % PAML 681 and 20 weight % Vitamin E acetate showed the highest deterrency.

The biological activity of synthetic PAML 681 was also evaluated in a feeding bioassay with a ladybird beetle. The bioassay was a choice test in which individual *H. axyridis* adults were presented with two offerings of an edible food item, for example, insect eggs of the moth *Uthesisia ornatrix*, of which one offering was treated by topical application of an ethyl ether solution of PAML 681, while the other offering ("control") was treated with ethyl ether only. Synthetic PAML 681 showed strong antifeedant activity against *H. axyridis*, indicated by a significant preference for control eggs over those treated with synthetic PAML 681.

Similar experiments were performed with synthetic samples of PAML 908 and PAML 1362, as well as with mixtures of PAML 681 and alpha-tocopherol acetate. All these PAML formulations likewise showed strong antifeedant activity, with highest activities observed for a composition comprising 80 weight % PAML 681 and 20 weight % alpha-tocopherol acetate.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A macrocycle compound having the formula:

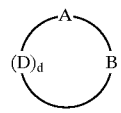

wherein d is an integer from 0 to about 100;

A, B, and each D are the same or different and are either

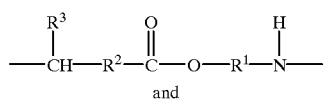

and

-continued

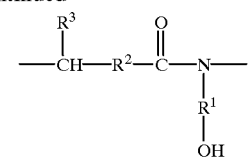

each $R^1$ is the same or different and is an alkylene moiety;
each $R^2$ is the same or different and is an alkylene moiety; and
each $R^3$ is the same or different and is either a hydrogen atom or an alkyl moiety.

2. A compound according to claim 1, wherein d is an integer from 0 to about 30.

3. A compound according to claim 1, wherein $R^3$ is a methyl group.

4. A compound according to claim 1, wherein each $R^1$ is the same or different and is a linear alkylene moiety having from about 1 to about 4 carbon atoms.

5. A compound according to claim 4, wherein each $R^1$ is the same or different and has the formula —$(CH_2)_n$—, where each n is the same or different and is an integer from about 1 to about 4.

6. A compound according to claim 5, each $R^1$ is the same and has the formula —$CH_2CH_2$—.

7. A compound according to claim 1, wherein each $R^2$ is the same or different and is a linear alkylene moiety having from about 4 to about 10 carbon atoms.

8. A compound according to claim 1, wherein each $R^2$ is the same or different and has the formula —$(CH_2)_m$—, where each m is the same or different and is an integer from about 4 to about 10.

9. A compound according to claim 8, wherein m is the same or different and is an integer from about 6 to about 8.

10. A compound according to claim 1, wherein each $R^3$ is the same or different and has the formula —$(CH_2)_rCH_3$, where each r is the same or different and is an integer from about 1 to about 5.

11. A compound according to claim 1, wherein A, B, and each D are the same or different and have the formula:

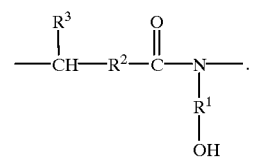

12. A compound according to claim 11, wherein each $R^1$ is —$(CH_2)_8$—, each $R^2$ is —$CH_2CH_2$—, and each $R^3$ is $CH_3$.

13. A compound according to claim 1, wherein A, B, and each D are the same or different and have the formula:

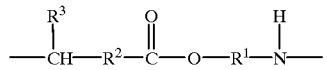

14. A compound according to claim 13, wherein each $R^1$ is —$(CH_2)_8$—, each $R^2$ is —$CH_2CH_2$—, and each $R^3$ is $CH_3$.

15. A compound according to claim 1, wherein said macrocycle is substantially pure.

16. A method of preparing a macrocycle compound having the formula:

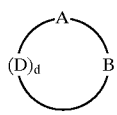

wherein
d is an integer from 0 to about 100;
A, B, and each D are the same or different and are:

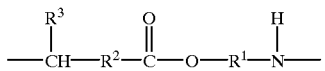

each $R^1$ is the same or different and is an alkylene moiety;
each $R^2$ is the same or different and is an alkylene moiety; and
each $R^3$ is the same or different and is either a hydrogen atom or an alkyl moiety;
said method comprising:
providing a linear compound having the formula:

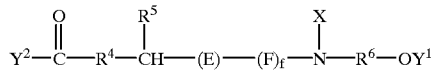

wherein
f is an integer from 0 to about 100;
E and each F are the same or different and are:

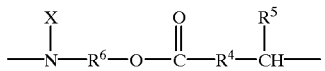

each $R^4$ is the same or different and is an alkylene moiety;
each $R^5$ is the same or different and is either a hydrogen atom or an alkyl moiety;
each $R^6$ is the same or different and is an alkylene moiety;
each X is the same or different and is either a hydrogen atom or an amine protecting group;
$Y^1$ is a hydrogen atom or a alcohol protecting group; and
$Y^2$ is an OH group or a carboxylic acid protecting group; and
cyclizing the linear compound under conditions effective to produce the macrocycle.

17. A method according to claim 16, wherein d is from about 1 to about 30.

18. A method according to claim 16, wherein at least one of A, B, or at least one D has the formula:

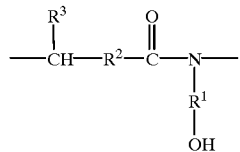

said method further comprising:
treating the macrocycle under conditions effective to cause at least one O-to-N acyl transfer.

19. A method according to claim 16, wherein said providing a linear compound comprises:

providing linear monomers which are the same or different and which have the formula:

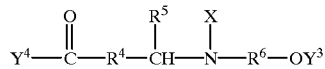

wherein
each $R^4$ is the same or different and is an alkylene moiety;
each $R^5$ is the same or different and is either a hydrogen atom or an alkyl moiety;
each $R^6$ is the same or different and is an alkylene moiety;
each X is the same or different and is either a hydrogen atom or an amine protecting group;
each $Y^3$ is the same or different and is either a hydrogen atom or an alcohol protecting group; and
each $Y^4$ is the same or different and is either an OH moiety or a carboxylic acid protecting group; and
reacting the linear monomers under conditions effective to produce the linear compound.

20. A composition comprising at least two of the macrocycles according to claim 1, wherein the at least two macrocycles are different from each other.

21. An arthropod repellent comprising:
at least one macrocycle according to claim 1; and
an additive for the at least one macrocycle.

22. An arthropod repellent according to claim 21, wherein the additive is a carrier, an acidic stabilizer, an antioxidant, or a combination thereof.

23. An arthropod repellent according to claim 22, wherein the acidic stabilizer is an organic acid, and inorganic acid, an acidic buffer system, or a combination thereof.

24. An arthropod repellent according to claim 23, wherein the antioxidant is a tocopherol.

25. An arthropod repellent according to claim 23, wherein the tocopherol is Vitamin E, a tocopherol acetate, ascorbic acid, or a combination thereof.

26. An arthropod repellent according to claim 23, wherein the tocopherol is Vitamin E acetate or alpha-tocopherol acetate.

27. A method for repelling arthropods from a location comprising:
disposing at least one macrocycle according to claim 1 proximate to the location.

28. A method according to claim 27, wherein the location is a bodily surface of an animal.

29. A method according to claim 28, wherein the animal is a human.

30. A method according to claim 27, wherein the location is a plant.

31. A method according to claim 27, wherein the location is a fruit or vegetable.

32. A method according to claim 27, wherein the location is a food storage location.

33. A method for disrupting mating of arthropods comprising:
exposing the arthropods or insects to the macrocycle according to claim 1.

34. A method according to claim 33, wherein said exposing is carried out at a particular location and wherein said method further comprises:
attracting the arthropods to the particular location respectively with an arthropod attractant prior to said exposing.

* * * * *